US008986929B2

(12) United States Patent
Lerer et al.

(10) Patent No.: US 8,986,929 B2
(45) Date of Patent: Mar. 24, 2015

(54) RGS2 GENOTYPES ASSOCIATED WITH EXTRAPYRAMIDAL SYMPTOMS INDUCED BY ANTIPSYCHOTIC MEDICATION

(75) Inventors: Bernard Lerer, Alon Shvut (IL); Lior Greenbaum, Yehud (IL)

(73) Assignee: Hadasit Medical Research Services and Development Ltd., Jerusalem (IL)

( * ) Notice: Subject to any disclaimer, the term of this patent is extended or adjusted under 35 U.S.C. 154(b) by 0 days.

(21) Appl. No.: 13/155,199

(22) Filed: Jun. 7, 2011

(65) Prior Publication Data

US 2011/0236896 A1   Sep. 29, 2011

Related U.S. Application Data

(63) Continuation of application No. 12/304,430, filed as application No. PCT/IL2007/000704 on Jun. 12, 2007, now abandoned.

(60) Provisional application No. 60/812,599, filed on Jun. 12, 2006.

(51) Int. Cl.
*C12Q 1/68* (2006.01)
*C12P 19/34* (2006.01)

(52) U.S. Cl.
CPC ........ *C12Q 1/6883* (2013.01); *C12Q 2600/156* (2013.01); *C12Q 2600/16* (2013.01); *C12Q 2600/172* (2013.01); *C12Q 2600/106* (2013.01)
USPC .......................... 435/6.1; 435/91.2; 424/146.1

(58) Field of Classification Search
CPC ........... C12Q 1/6883; C12Q 2600/106; C12Q 2600/156; C12Q 2600/172; C12Q 1/68; C12Q 2600/118
See application file for complete search history.

(56) References Cited

U.S. PATENT DOCUMENTS

| | | | |
|---|---|---|---|
| 3,539,573 A | 11/1970 | Schmutz et al. | 260/268 |
| 4,086,350 A | 4/1978 | Zirkle | 424/267 |
| 4,458,066 A | 7/1984 | Caruthers et al. | 536/27 |
| 4,710,500 A | 12/1987 | Perregaard | 514/254 |
| 4,804,663 A | 2/1989 | Kennis et al. | 514/258 |
| 4,831,031 A | 5/1989 | Lowe, III et al. | 514/254 |
| 4,879,288 A | 11/1989 | Warawa et al. | 514/211 |
| 5,006,528 A | 4/1991 | Oshiro et al. | 514/253 |
| 5,112,838 A | 5/1992 | Perregaard et al. | 514/323 |

(Continued)

FOREIGN PATENT DOCUMENTS

| | | |
|---|---|---|
| WO | WO 89/11548 | 11/1989 |
| WO | 2007/144874 | 12/2007 |

OTHER PUBLICATIONS

Koning J.P. et al. Pschopharmacology (2012) vol. 219, pp. 727-736.*

(Continued)

*Primary Examiner* — Stephen Kapushoc
(74) *Attorney, Agent, or Firm* — Winston & Shrawn LLP

(57) ABSTRACT

The present invention identifies genotypes associated with resistance to extrapyramidal symptoms induced by antipsychotic drugs. The present invention further identifies genotypes associated with predisposition to the onset or aggravation of extrapyramidal symptoms induced by antipsychotic drugs and use thereof for assessment of patient populations. Specifically, the present invention relates to particular polymorphisms in the RGS2 gene that are associated with resistance or susceptibility to drug-induced extrapyramidal symptoms.

11 Claims, 2 Drawing Sheets

(56) References Cited

U.S. PATENT DOCUMENTS

| | | | |
|---|---|---|---|
| 5,137,712 A | 8/1992 | Kask et al. | 424/10 |
| 5,229,382 A | 7/1993 | Chakrabarti et al. | 514/220 |
| 5,238,945 A | 8/1993 | Perregaard et al. | 514/323 |
| 5,312,925 A | 5/1994 | Allen et al. | 544/368 |
| 5,348,855 A | 9/1994 | Dattagupta et al. | 435/6 |
| 5,498,324 A | 3/1996 | Yeung et al. | 204/452 |
| 5,500,343 A | 3/1996 | Blum et al. | 435/6 |
| 5,593,840 A | 1/1997 | Bhatnagar et al. | 435/6 |
| 6,844,154 B2 | 1/2005 | Landers | 435/6 |
| 6,951,721 B2 | 10/2005 | Murphy | 435/6 |
| 6,977,257 B2 | 12/2005 | Parab | 514/253.07 |
| 7,041,810 B2 | 5/2006 | Small et al. | |
| 2003/0119716 A1 | 6/2003 | Ho et al. | 514/1 |
| 2006/0252103 A1 | 11/2006 | Panicker et al. | |
| 2009/0307179 A1 | 12/2009 | Colby et al. | |
| 2009/0307180 A1 | 12/2009 | Colby et al. | |
| 2009/0307181 A1 | 12/2009 | Colby et al. | |
| 2010/0021891 A1 | 1/2010 | Lerer et al. | |

OTHER PUBLICATIONS

Higa M. et al. Neuroscience Letter (2010) vol. 469, pp. 55-59.*
Al Hadithy A.F. et al. Human Psychopharmacology (2009) vol. 24, pp. 123-128.*
International Search Report PCT/IL2007/000704 Dated Oct. 10, 2007.
Berman D.M. Cancer Research, vol. 64 (Sep. 15, 2004) pp. 6820-6826.
Bernstein, Leah S. et al, "RGS2 Binds Directly and Selectively to the M1 Muscarinic Acetylcholine Receptor Third Intracellular Loop to Modulate $G_{q/11}\alpha$ Signaling", J Biol Chem., vol. 279(20), pp. 21248-21256 (2004).
Chowdari, Kodavali V. et al., "Association and linkage analyses of RGS4 polymorphisms in schizophrenia. Hum Mol Genet.", vol. 11(12), pp. 1373-1380 (2002).
Conner, Brenda J. et al., "Detection of sickle cell beta S-globin allele by hybridization with synthetic oligonucleotides", Proc Natl Acad Sci USA, vol. 80(1), pp. 278-282 (1983).
Fatemi, S. Hossein et al., (XP-002450236) "Chronic Olanzapine Treatment Causes Differential Expression of Genes in Frontal Cortex of Rats As Revealed by DNA Microarray Technique", Neuropsychopharmacology, vol. 31, No. 9, Nature Publishing Group ©, pp. 1888-1899 (2006).
Gabriel, Stacey B. et al., "The structure of haplotype blocks in the human genome", Science, vol. 296(5576), pp. 2225-2229 (2002).
Geurts, Muriel et al., "Altered expression of regulators of G-protein signaling (RGS) mRNAs in the striatum of rats undergoing dopamine depletion", Biochem Pharmacol. vol. 66(7), pp. 1163-1170 (2003).
Ghavami, Afshin et al., "Differential effects of regulator of G protein signaling (RGS) proteins on serotonin 5-HT1A, 5-HT2A, and dopamine D2 receptor-mediated signaling and adenylyl cyclase activity", Cell Signal, vol. 16(6), pp. 711-721 (2004).
Greenbaum, L. et al. (XP009089245) Association of the RGS2 Gene With Extrapyramidal Symptoms Induced by Treatment With Antipsychotic Medication, Pharmacogenetics and Genomics, vol. 17, No. 7, Lippincott Williams & Wilkins ©, pp. 519-528, (2007).
Hegele R.A. Arterioscler Thromb Vasc Biol. 2002;22:1058-1061.
Ingi, Tatsuya et al., "Dynamic Regulation of RGS2 Suggests a Novel Mechanism in G-Protein Signaling and Neuronal Plasticity", J. Neurosci., vol. 18(18), pp. 7178-7188 (1998).
Juppner H. Bone (Aug. 1995) vol. 17, No. 2, Supplement, pp. 39S-42S.
Kaiser, R. et al., (XP-002450237) "Relationship Between Adverse Effects of Antipsychotic Treatment and Dopamine $D_2$ Receptor Polymorphisms in Patients With Schizophrenia", Molecular Psychiatry, vol. 7, No. 7, Nature Publishing Group ©, pp. 695-705 (2002).
Kirchheiner, J. et al., "Phamacogenetics of antidepressants and antipsychotics: the contribution of allelic variations to the phenotype of drug response", Mol Psychiatry, vol. 9(5), pp. 442-473 (2004).
Larminie, Christopher et al., "Selective expression of regulators of G-protein signaling (RGS) in the human central nervous system", Mol Brain Res., vol. 122(1), pp. 24-34 (2004).
Leygraf, A. et al., "Rgs 2 gene polymorphisms as modulators of anxiety in humans?", J. Neural Transm., vol. 113(12), pp. 1921-1925 (2006).
Pennsis E. Science (Sep. 18, 1998) vol. 281, pp. 1787-1789.
Robinet, E.A. et al. (XP-002450235) "Chronic Treatment With Certain Antipsychotic Drugs Preserves Upregulation of Regulator of G-Protein Signalling 2 mRNA in Rat Striatum as Opposed to C-Fos mRNA", Neuroscience Letters, vol. 307, No. 1, Elsevier Science Ireland Ltd. ©, pp. 45-48 (2001).
Taymans, Jean-Marc et al.; "Striatal gene expression of RGS2 and RGS4 is specifically mediated by dopamine D1 and D2 receptors: clues for RGS2 and RGS4 functions", J Neurochem., vol. 84(5), pp. 1118-1127 (2003).
Taymans, Jean-Marc et al., "Dopamine receptor-mediated regulation of RGS2 and RGS4 mRNA differentially depends on ascending dopamine projections and time", Eur J Neurosci., vol. 19(8), pp. 2249-2260 (2004).
Thisted R.A. What is a P-value? (May 25, 1998), from www.statuchicago.eduhthisted, printed pp. 1-6.
Blanchet, P. J., "Antipsychotic Drug-Induced Movement Disorders", Can. J. Neurol. Sci. 30 (Suppl 1):S101-S107 (2003).
Casey, D. E., "Pathophysiology of Antipsychotic Drug-Induced Movement Disorders", *Clin. Psychiatry* 65 Suppl 9:25-28 (2004).
Greenbaum, L. et al., "Further Evidence for Association of the RGS2 Gene With Antipsychotic-Induced Parkinsonism: Protective Role of a Functional Polymorphism in the 3'-Untranslated Region", The *Pharmacogenomics Journal* 9 (2):103-110 Epub Mar. 18, 2008 (2009).
Miyamoto, S. et al., "Treatments for Schizophrenia: A Critical Review of Pharmacology and Mechanisms of Action of Antipsychotic Drugs", *Molecular Psychiatry*, 10(1):79-104 (2005).
Al Hadithy et al., (2008) Pharmacogenetics of parkinsonism, rigidity, rest tremor, and bradykinesia in African-Caribbean inpatients: differences in association with dopamine and serotonin receptors. Am J Med Genet B Neuropsychiatr Genet 147B(6): 890-897.
Alkelai and Greenbaum (2009) Genome-wide association study of antipsychotic-induced parkinsonism severity among schizophrenia patients. Psychopharmacology (Berl) 206(3): 491-499.
Alkelai et al., (2012) Association of the Type 2 diabetes mellitus susceptibility gene, TCF7L2, with schizophrenia in an Arab-Israeli family sample. PlosOne 7(1): e29228-1-222928-8.
Beaucage and Caruthers (1981) Deoxynucleoside phosphoramidites—A new class of key intermediates for deoxypolynucleotide synthesis. Tetrahedron Letters 22(20): 1859-1862.
Beaulieu et al., (2005) An Akt/beta-arrestin 2/PP2A signaling complex mediates dopaminergic neurotransmission and behavior. Cell 122(2): 261-273.
Caligiuri et al., (1993) Parkinsonism in neuroleptic-naive schizophrenic patients. Am J Psychiatry 150(9): 1343-1348.
Crowley et al., (2009) Pharmacogenomic genome-wide association studies: lessons learned thus far. Pharmacogenomics 10(2): 161-163.
Goldstein and Weale (2001) Population genomics: linkage disequilibrium holds the key. Curr Biol 11(14): R576-R579.
Greenbaum et al., (2012) Association of the ZFPM2 gene with antipsychotic-induced parkinsonism in schizophrenia patients. Psychopharmacology (Berl) 220(3): 519-528.
Gunes et al., (2008) Further evidence for the association between 5-HT2C receptor gene polymorphisms and extrapyramidal side effects in male schizophrenic patients. Eur J Clin Pharmacol 64(5): 477-482.
Hirose (2006) Drug induced parkinsonism. J Neurol 253 (Suppl 3): III/22-III/24.
Hoh et al., (2003) SNP haplotype tagging from DNA pools of two individuals. BMC Bioinformatics 4: 1-5.
Hollinger and Hepler (2002) Cellular regulation of RGS proteins: modulators and integrators of G protein signaling. Pharmacol Rev 54(3): 527-559.
Janno et al., (2004) Prevalence of neuroleptic-induced movement disorders in chronic schizophrenia inpatients. Am J Psychiatry 161(1): 160-163.

(56) References Cited

OTHER PUBLICATIONS

Kay et al., (1987) The positive and negative syndrome scale (PANSS) for schizophrenia. Schizophr Bull 13(2): 261-276.

Kindmark et al., (2008) Genome-wide pharmacogenetic investigation of a hepatic adverse event without clinical signs of immunopathology suggests an underlying immune pathogenesis. Pharmacogenomics J 8(3): 186-195.

Kovoor et al., (2005) D2 dopamine receptors colocalize regulator of G-protein signaling 9-2 (RGS9-2) via the RGS9 DEP domain, and RGS9 knock-out mice develop dyskinesias associated with dopamine pathways. J Neurosci 25(8): 2157-2165.

Landegren et al., (1988) A ligase-mediated gene detection technique. Science 241(4869): 1077-1080.

Landegren et al., (1988) DNA diagnostics—molecular techniques and automation. Science 242(4876): 229-237.

Lerner et al., (2007) The prevalence of neuroleptic drug-induced tardive movement subsyndromes among schizophrenic and schizoaffective patients residing in the southern region of Israel. Isr J Psychiatry Relat Sci 44(1): 20-28.

Lieberman et al., (2005) Effectiveness of antipsychotic drugs in patients with chronic schizophrenia. N Engl J Med 353 (12): 1209-1223.

Little et al., (1997) Detection of RET proto-oncogene codon 634 mutations using mass spectrometry. J Mol Med (Berl) 75(10): 745-750.

Little et al., (1997) Identification of apolipoprotein E polymorphisms using temperature cycled primer oligo base extension and mass spectrometry. Eur J Clin Chem Clin Biochem 35(7): 545-548.

Liu et al., (2009) Genome-wide association analyses suggested a novel mechanism for smoking behavior regulated by IL15. Mol Psychiatry 14(7): 668-680.

Maxam and Gilbert (1980) Sequencing end-labeled DNA with base-specific chemical cleavages. Methods Enzymol 65 (1): 499-560.

McCreadie et al., (1996) Abnormal movements in never-medicated Indian patients with schizophrenia. Br J Psychiatry 168(2): 221-226.

McCullough et al., (2005) High-throughput alternative splicing quantification by primer extension and matrix-assisted laser desorption/ionization time-of-flight mass spectrometry. Nucleic Acids Res 33(11): e99-1-e99-9.

Price et al., (2006) Principal components analysis corrects for stratification in genome-wide association studies. Nat Genet 38(8): 904-909.

Pritchard and Przeworski (2001) Linkage disequilibrium in humans: models and data. Am J Hum Genet 69(1): 1-14.

Purcell et al., (2007) PLINK: a tool set for whole-genome association and population-based linkage analyses. Am J Hum Genet 81(3): 559-575.

Saiki et al., (1985) A novel method for the detection of polymorphic restriction sites by cleavage of oligonucleotide probes: application to sickle-cell anemia. Nature Biotechnology 3(11): 1008-1012.

Sanger et al., (1977) DNA sequencing with chain-terminating inhibitors. Proc Natl Acad Sci U S A 74(12): 5463-5467.

Simpson and Angus (1970) A rating scale for extrapyramidal side effects. Acta Psychiatr Scand Suppl 212: 11-19.

Smith et al., (2005) Clozapine, risperidone, olanzapine, and conventional antipsychotic drug effects on glucose, lipids, and leptin in schizophrenic patients. Int J Neuropsychopharmacol 8(2): 183-194.

Stephens and Donnelly (2003) A comparison of bayesian methods for haplotype reconstruction from population genotype data. Am J Hum Genet 73(5): 1162-1169.

Stephens et al., (2001) A new statistical method for haplotype reconstruction from population data. Am J Hum Genet 68(4): 978-989.

Sullivan et al., (2008) Genomewide association for schizophrenia in the CATIE study: results of stage 1. Mol Psychiatry 13(6): 570-584.

Van der oord et al., (2008) Genomewide association analysis followed by a replication study implicates a novel candidate gene for neuroticism. Arch Gen Psychiatry 65(9): 1062-1071.

RefSNP Cluster report rs 12678719 (available at ncbi.nlm.nih.gov/projects/SNP, printed Nov. 19, 2013, pp. 1-7.

Greenbaum, Lior et al., "Alteration in RGS2 expression level is associated with changes in haloperidol induced extrapyramidal features in a mutant mouse model", European Neuropsychopharmacology, doi:10.1016/j.euroneuro.2011.09.006 (2011).

Semplicini, Andrea et al., "Reduced expression of regulator of G-protein signaling 2(RGS2) in hypertensive patients increases calcium mobilization and ERK1/2 phosphorylation induced by angiotensin II", J. Hypertens, vol. 24, No. 6, pp. 1115-1124 (2006).

* cited by examiner

SEQUENCE LISTING

<160> NUMBER OF SEQ ID NOS: 24

<210> SEQ ID NO 1
<211> LENGTH: 21

```
<212> TYPE: DNA
<213> ORGANISM: Artificial
<220> FEATURE:
<223> OTHER INFORMATION: SNP containing sequence

<400> SEQUENCE: 1
gaatttatgg gagtggatag t                                              21

<210> SEQ ID NO 2
<211> LENGTH: 21
<212> TYPE: DNA
<213> ORGANISM: Artificial
<220> FEATURE:
<223> OTHER INFORMATION: SNP containing sequence

<400> SEQUENCE: 2
tccagccctg tggccagcct c                                              21

<210> SEQ ID NO 3
<211> LENGTH: 21
<212> TYPE: DNA
<213> ORGANISM: Artificial
<220> FEATURE:
<223> OTHER INFORMATION: SNP containing sequence

<400> SEQUENCE: 3
ttggtaaaaa tgcgttcagc t                                              21

<210> SEQ ID NO 4
<211> LENGTH: 21
<212> TYPE: DNA
<213> ORGANISM: Artificial
<220> FEATURE:
<223> OTHER INFORMATION: SNP containing sequence

<400> SEQUENCE: 4
ctatgtgcaa cggtattgaa g                                              21

<210> SEQ ID NO 5
<211> LENGTH: 21
<212> TYPE: DNA
<213> ORGANISM: Artificial
<220> FEATURE:
<223> OTHER INFORMATION: SNP containing sequence

<400> SEQUENCE: 5
gaaataaata taccaaatta a                                              21

<210> SEQ ID NO 6
<211> LENGTH: 21
<212> TYPE: DNA
<213> ORGANISM: Artificial
<220> FEATURE:
<223> OTHER INFORMATION: SNP containing sequence

<400> SEQUENCE: 6
cttactgtac atgccacaga a                                              21

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7
```
acgttggatg cagtatacag atcacacctg                              30

<210> SEQ ID NO 8
<211> LENGTH: 30
<212> TYPE: DNA
<213> ORGANISM: Artificial
<220> FEATURE:
<223> OTHER INFORMATION: Primer

<400> SEQUENCE: 8
acgttggatg cgctcaactg ttgaagttcc                              30

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
ttctgcagat ttactatcca ct                                      22

<210> SEQ ID NO 10
<211> LENGTH: 30
<212> TYPE: DNA
<213> ORGANISM: Artificial
<220> FEATURE:
<223> OTHER INFORMATION: Primer

<400> SEQUENCE: 10
acgttggatg tgagctcttg gtggaatctg                              30

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
acgttggatg ctgtagattc tagccttggg                              30

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
cctttcatag tccagccctg                                         20

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
acgttggatg gcaacacttg aatatgctac                              30

<210> SEQ ID NO 14
<211> LENGTH: 30
<212> TYPE: DNA
<213> ORGANISM: Artificial

<220> FEATURE:
<223> OTHER INFORMATION: Primer

<400> SEQUENCE: 14
acgttggatg tgccttatgc ggtttgtctc         30

<210> SEQ ID NO 15
<211> LENGTH: 23
<212> TYPE: DNA
<213> ORGANISM: Artificial
<220> FEATURE:
<223> OTHER INFORMATION: Primer

<400> SEQUENCE: 15
tgggtgactt tatttggtaa aaa                23

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
acgttggatg agtactgatg atctgtggtc         30

<210> SEQ ID NO 17
<211> LENGTH: 31
<212> TYPE: DNA
<213> ORGANISM: Artificial
<220> FEATURE:
<223> OTHER INFORMATION: Primer

<400> SEQUENCE: 17
acgttggatg ggattcagta acagtgaagt g        31

<210> SEQ ID NO 18
<211> LENGTH: 23
<212> TYPE: DNA
<213> ORGANISM: Artificial
<220> FEATURE:
<223> OTHER INFORMATION: Primer

<400> SEQUENCE: 18
agtgaagtgt ttactatgtg caa                23

<210> SEQ ID NO 19
<211> LENGTH: 30
<212> TYPE: DNA
<213> ORGANISM: Artificial
<220> FEATURE:
<223> OTHER INFORMATION: Primer

<400> SEQUENCE: 19
acgttggatg agcaatcata gctcacactc         30

<210> SEQ ID NO 20
<211> LENGTH: 30
<212> TYPE: DNA
<213> ORGANISM: Artificial
<220> FEATURE:
<223> OTHER INFORMATION: Primer

<400> SEQUENCE: 20
acgttggatg cctatcctcc aagaagtacc         30

-continued

```
<210> SEQ ID NO 21
<211> LENGTH: 25
<212> TYPE: DNA
<213> ORGANISM: Artificial
<220> FEATURE:
<223> OTHER INFORMATION: Primer

<400> SEQUENCE: 21
aattaagtag ctgatgaaat aaata                                              25

<210> SEQ ID NO 22
<211> LENGTH: 30
<212> TYPE: DNA
<213> ORGANISM: Artificial
<220> FEATURE:
<223> OTHER INFORMATION: Primer

<400> SEQUENCE: 22
acgttggatg agcattcctg atatcagcac                                         30

<210> SEQ ID NO 23
<211> LENGTH: 30
<212> TYPE: DNA
<213> ORGANISM: Artificial
<220> FEATURE:
<223> OTHER INFORMATION: Primer

<400> SEQUENCE: 23
acgttggatg gcacagtgca tacaaaacac                                         30

<210> SEQ ID NO 24
<211> LENGTH: 22
<212> TYPE: DNA
<213> ORGANISM: Artificial
<220> FEATURE:
<223> OTHER INFORMATION: Primer

<400> SEQUENCE: 24
gttaagagga aattctgtgg ca                                                 22
```

RGS2 GENOTYPES ASSOCIATED WITH EXTRAPYRAMIDAL SYMPTOMS INDUCED BY ANTIPSYCHOTIC MEDICATION

This application is a continuation of application Ser. No. 12/304,430 filed Jul. 10, 2009 now abandoned which is the 371 filing of International Patent Application PCT/IL2007/000704 filed Jun. 12, 2007, which claims the benefit of application No. 60/812,599 filed Jun. 12, 2006.

FIELD OF THE INVENTION

The present invention relates to genotypes associated with resistance or susceptibility to extrapyramidal symptoms induced by antipsychotic drugs and use thereof for assessment of patient populations. In particular, the present invention relates to polymorphisms in the RGS2 gene that are associated with resistance or susceptibility to drug-induced extrapyramidal symptoms.

BACKGROUND OF THE INVENTION

Psychoses are serious mental illnesses characterized by defective or lost contact with reality. Psychotic patients may suffer hallucinations and delusions as part of their disease. Psychoses exact a tremendous emotional and economic toll on patients, their families, and society as a whole. While the mechanisms underlying these diverse disease states are poorly understood, there are extensive efforts devoted to the discovery of therapies that may offer new hope for the treatment of psychotic patients.

Typical antipsychotic drugs, also called first generation or traditional antipsychotics, and atypical antipsychotic drugs (also called second generation antipsychotics) are indispensable in the pharmacological treatment of psychoses, such as schizophrenia and other neuropsychiatric conditions that are associated with psychotic states. Typical antipsychotic drugs include haloperidol, penfluridol, sulpiride, zuclopenthixol, flupenthixol, clotiapine and phenothiazines, such as chlorpromazine, prochlorperazine, flupenazine, trifluoperazine, perphenazine, levomepromazine and thioridazine, among others. The most common side effects associated with use of typical antipsychotics are extrapyramidal symptoms (EPS), particularly, dystonia (abnormal tonicity of the muscles), Parkinsonism and akathisia (motor restlessness). EPS may develop within hours to days of the implementation of treatment. Longer-term treatment is associated with development of the chronic, choreoathetotic movement disorder, tardive dyskinesia. The unpleasant side effects induced by antipsychotics often lead patients to stop using them.

Progress in the treatment of psychotic conditions has been achieved through the introduction of atypical antipsychotic agents (also known as second generation antipsychotics), which have a significantly decreased propensity to cause extrapyramidal side effects. Atypical antipsychotics include, but are not limited to: clozapine, risperidone, olanzapine, sertindole, quetiapine, and ziprasidone. While the side effect profile of these atypical antipsychotics is superior to that of typical agents with regard to EPS, treatment with these new drugs alone does not provide total relief to every psychotic patient. Improvement in the clinical efficacy of atypical antipsychotics is achieved, in certain patients, by combining these drugs with other antipsychotics, including typical antipsychotics, thereby exposing patients to onset or worsening of EPS.

The pathophysiology of EPS induced by antipsychotic drugs is still unclear. However, the most plausible explanation relates to the dopamine D2 receptor, the activity of which is mediated by two major classes of heterotrimeric G protein coupled receptors (GPCR). GPCR signaling is regulated by the regulators of G-protein signaling (RGS) proteins (Ingi et al., J Neurosci., 1998; 18:7178-88). RGS2 protein belongs to the B/R4 subfamily of RGS proteins (which also includes RGS1-5, RGS8, RGS13, RGS16 and RGS18). RGS mediate the activity of GTPase-accelerating proteins (GAP) and their interaction with G-alpha subunits (Hollinger and Hepler, Pharmacol Rev., 2002; 54:527-59). Among G protein coupled receptors whose signaling is reported to be influenced by RGS2 are the dopamine D1 receptor (Taymans et al., J Neurochem., 2003; 84:1118-27) and the 5-HT2A receptor (Ghavami et al., Cell Signal, 2004; 16:711-21).

SNPs in the RGS2 gene, including inter alia rs2746073 and rs4606, and haplotypes comprising same were shown to be associated with panic disorders (Leygraft et al., J. Neural Transm., Jun. 1, 2006; PMID: 16736243). The presence of a particular human D2 receptor gene allele was found to correlate with susceptibility to compulsive disorder, as disclosed in U.S. Pat. No. 5,500,343. However, nowhere in the background art is it taught or suggested that single nucleotide polymorphisms (SNPs) or haplotypes in RGS genes can indicate the susceptibility of a subject to develop EPS or to suffer from enhanced EPS during treatment with psychotic drugs.

An assay for predicting the potential ability of a drug to cause EPS in rats is disclosed in U.S. Pat. No. 4,086,350. The assay is based on calculating the ratio of the drug's $ED_{50}$ (i.p.) for antagonism of amphetamine-induced rotation to the drug's $ED_{50}$ (i.p.) for blockade of shock avoidance acquisition. This assay is suitable for application in laboratory animals.

A method for reversing or preventing extrapyramidal side effects in a human due to neuroleptic treatment is disclosed in U.S. Pat. No. 5,137,712. The method comprises concurrently administering to said human said neuroleptic and an effective amount of S-adenosyl-L-methionine or a physiologically acceptable salt thereof.

The aforementioned methods do not meet the requirement to determine susceptibility to EPS before initiation of the antipsychotic treatment. Such assessment of patients at risk for EPS is essential for optimization of antipsychotic treatment regimen.

SUMMARY OF THE INVENTION

The present invention provides methods for assessment of the propensity to develop extrapyramidal symptoms (EPS) or for EPS to worsen during treatment with antipsychotic drugs. In particular, the present invention provides methods for assessing patient population for susceptibility to adverse effects of antipsychotic drugs.

The method of the invention is based in part on the unexpected discovery that specific SNPs and haplotypes in the RGS2 gene are associated with resistance to the development of EPS during treatment with typical antipsychotics, while other SNPs and haplotypes in the RGS2 gene correlate with onset or worsening of EPS upon treatment with typical antipsychotic drugs. These correlations were found to be independent of treatment regimen in terms of dose and type of antipsychotic drug. In addition, the SNPs and haplotypes in the RGS2 gene that were associated with resistance to or emergence of EPS, do not alter the structure of the RGS2 protein and are not known to influence its function. The unexpected findings of the present invention indicate that the presence of specific SNPs and haplotypes in the RGS2 gene can be used to predict resistance to EPS and thus to design a treatment regimen which includes typical antipsychotics. Furthermore, the SNPs and haplotypes in the RGS2 gene that were found to correlate significantly with susceptibility to development or aggravation of EPS can be used to design a treatment regimen.

According to one aspect, the present invention provides a method for assessing a tendency of a subject to develop extrapyramidal symptoms following treatment with an antipsychotic drug, comprising:

(a) obtaining a sample comprising genetic material from the subject;

(a) determining, in the genetic material, the nucleotide sequence of the RGS2 gene or a fragment thereof;

(b) identifying in said nucleotide sequence at least one polymorphic site within said RGS2 gene or fragment thereof, wherein the identity of the at least one polymorphic site is indicative of the tendency to develop at least one extrapyramidal symptom following treatment with antipsychotic drugs.

As used herein, the term "develop" encompasses the emergence and/or aggravation of the extrapyramidal symptoms (EPS) following treatment with an antipsychotic drug, such that these terms are used herein interchangeably.

According to certain embodiments, the at least one polymorphic site has a reference sequence number on chromosome 1 selected from the group consisting of rs2179652, rs1933695, rs2746073, rs4606, rs1819741 and rs1152746.

According to other embodiments, the presence of at least one of thymine at rs2179652, guanine at rs1933695, adenine at rs2746073, guanine at rs4606, cytosine at rs1819741, and adenine at rs1152746, is indicative of resistance to emergence or aggravation of extrapyramidal symptoms following treatment with an antipsychotic drug.

According to one embodiment, the presence of at least one of: thymine at rs2179652 and guanine at rs1933695; thymine at rs2179652 and adenine at rs2746073; guanine at rs4606 and adenine at rs2746073; guanine at rs4606 and cytosine at rs1819741; and cytosine at rs1819741 and adenine at rs1152746 is indicative of resistance to emergence or aggravation of EPS following treatment with an antipsychotic drug.

According to another embodiment, the presence of guanine at rs1933695 and rs4606, thymine at rs2179652, cytosine at rs1819741 and adenine at rs1152746, is indicative of resistance to developing EPS.

According to certain currently preferred embodiments, the presence of guanine rs4606, thymine at rs2179652, cytosine at rs1819741 and adenine at rs1152746, is indicative of resistance to developing EPS.

According to further embodiments, the presence of at least one of: thymine at rs2746073, thymine at rs1819741, cytosine at rs2179652, cytosine at rs4606 and guanine at rs1152746, is indicative of susceptibility to emergence or aggravation of extrapyramidal symptoms following treatment with an antipsychotic drug.

According to one embodiment, the presence of at least one of: thymine at rs1819741 and guanine at rs1152746; thymine at rs1819741 and cytosine at rs4606; thymine at a rs1819741 and guanine at rs1933695; thymine at rs1819741 and cytosine at rs2179652; thymine at rs2746073 and cytosine at rs2179652; thymine at rs2746073 and cytosine at rs4606; and cytosine at rs2179652 and guanine at rs1933695, is indicative of susceptibility to emergence or aggravation of EPS following treatment with an antipsychotic drug.

According to another embodiment, the presence of guanine at rs1933695 and rs1152746, cytosine at rs2179652 and rs4606 and thymine at rs1819741, is indicative of susceptibility to developing EPS.

According to certain embodiments, the sample is obtained from a biological specimen selected from the group consisting of: blood, saliva, urine, sweat, buccal material, skin and hair.

Any method for determining nucleic acid sequence and for analyzing the identified nucleotides for polymorphism, known to a person skilled in the art, can be used according to the teachings of the present invention.

According to certain embodiments, identifying the at least one site of nucleotide polymorphism is attained by a technique selected from the group consisting of: terminator sequencing, restriction digestion, allele-specific polymerase reaction, single-stranded conformational polymorphism analysis, genetic bit analysis, temperature gradient gel electrophoresis, ligase chain reaction and ligase/polymerase genetic bit analysis.

According to yet another embodiment, the nucleotide polymorphism is identified by employing nucleotides with a detectable characteristic selected from the group consisting of inherent mass, electric charge, electric spin, mass tag, radioactive isotope type bioluminescent molecule, chemiluminescent molecule, hapten molecule, protein molecule, light scattering/phase shifting molecule and fluorescent molecule.

According to yet another embodiment, the subject in need thereof is psychotic. According to yet another embodiment, the method for diagnosing tendency to develop extrapyramidal symptoms is performed prior to initiation of treatment with an antipsychotic drug. According to additional embodiment, the method is performed after initiation of the treatment. According to yet another embodiment, the antipsychotic drug is selected from the group consisting of: zuclopenthixol, haloperidol, perphenazine, clotiapine, fluphenazine, flupenthixol, levomepromazine, chlorpromazine, sulpiride, penfluridol, pimozide, molindone, thiothixene, thioridazine, trifluoperazine, loxapine, prochlorperazine and combinations thereof. According to yet another embodiment, the antipsychotic drug treatment further comprises at least one atypical antipsychotic drug. According to a certain embodiment, the at least one atypical antipsychotic drug is risperidone.

According to yet another embodiment, the method further comprises repeating steps (b) and (c). According to yet another embodiment, the method further comprises amplifying said nucleotide sequence of the RGS2 gene or fragment thereof prior to step (c).

According to yet another embodiment, the at least one extrapyramidal symptom is selected from the group consisting of Parkinsonism, acute dystonia, dyskinesia, tardive dystonia and akathisia.

Other objects, features and advantages of the present invention will become clear from the following description and drawings.

DETAILED DESCRIPTION OF THE INVENTION

Definitions

Figure 1:
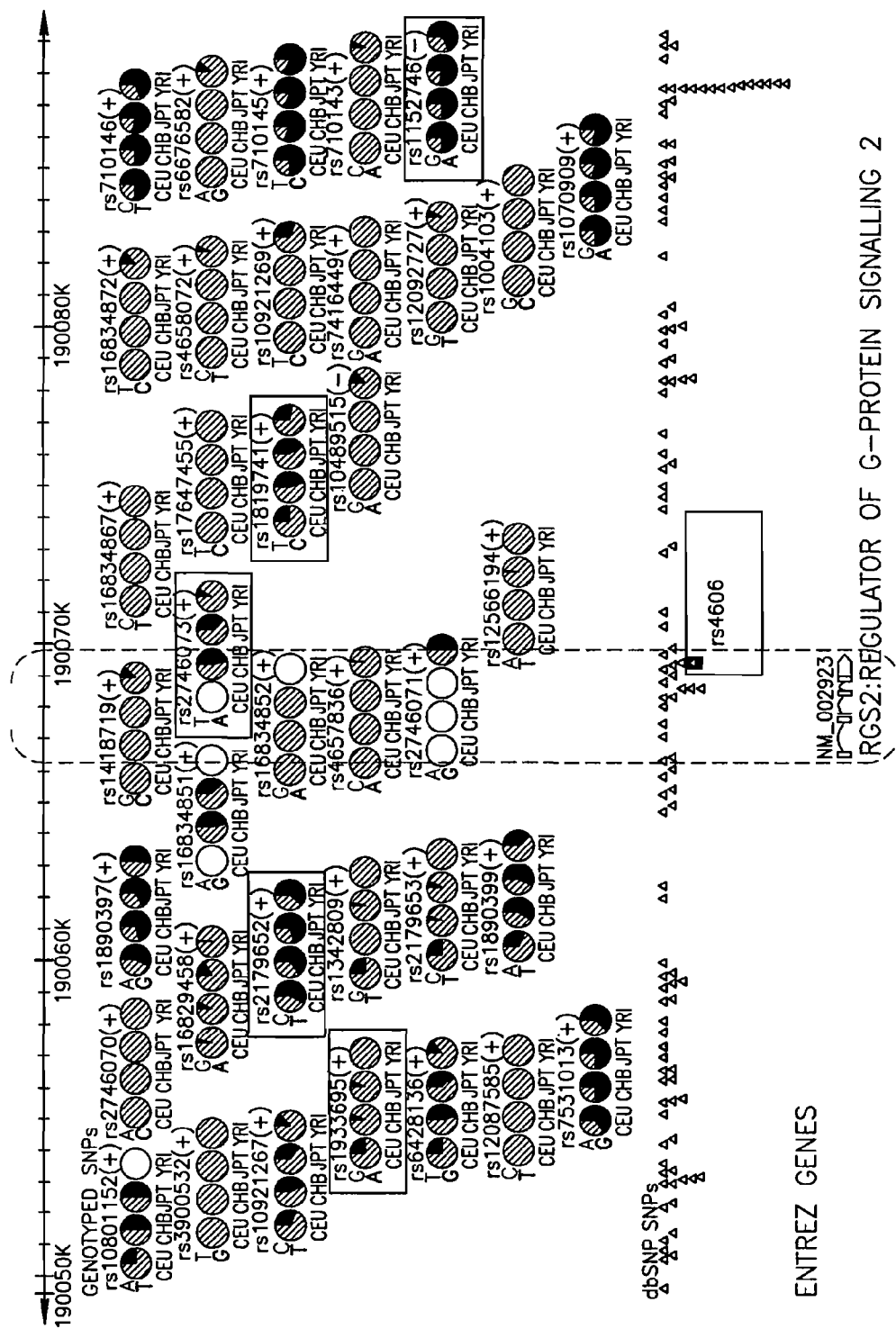
FIG. 1 shows SNP distribution on a 40 Kbp region spanned from nucleotide no. 189491443 to nucleotide no. 189531442 of chromosome 1 in the following populations: Yoruba in Ibadan, Nigeria (YRI); Japanese in Tokyo, Japan (JPT); Han Chinese in Beijing, China (CHB); Utah residents with ancestry from northern and western Europe (CEU/CEPH). The SNPs set forth in SEQ ID NO:1-6 are boxed. This region encompasses the RGS2 coding region at nucleotides 189509827 to 189513059 (within brackets).

As used herein, the term "gene" has its meaning as understood in the art. In general, a gene is taken to include gene regulatory sequences (e.g. promoters, enhancers, etc.) and/or intron sequences, in addition to coding sequences (open reading frames). It will further be appreciated that definitions of "gene" include references to nucleic acids that do not encode proteins but rather encode functional RNA molecules such as microRNAs (miRNAs), tRNAs, etc.

The term "allele" refers to an alternative version (i.e., nucleotide sequence) of a gene or DNA sequence at a specific chromosomal locus.

The term "polymorphism" as used herein refers to the occurrence of two or more alternative genomic sequences or alleles in a population. "Polymorphic" refers to the condition in which two or more variants of a specific genomic sequence can be found in a population. A "polymorphic site" is the locus at which the variation occurs. Polymorphism refers to the occurrence of two or more genetically determined alternative sequences or alleles in a population. Preferred polymorphisms have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTRs), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms. A triallelic polymorphism has three forms.

The terms "single nucleotide polymorphisms" or "SNPs" (pronounced "snips") are interchangeably used to describe particular DNA sequence variations that occur when a single nucleotide (A, T, C or G) in the genome sequence is altered. For example a SNP might change the DNA sequence A<u>A</u>GGCTAA to A<u>T</u>GGCTAA. For a variation to be considered a SNP, it must occur in at least 1% of the population. SNPs, which make up about 90% of all human genetic variation, occur every 100 to 300 bases along the 3-billion-base human genome. The site is usually preceded by and followed by highly conserved sequences of the allele (e.g., sequences that vary in less than 1/100 or 1/1000 members of the populations). A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele. It should be noted that a single nucleotide change could result in the destruction or creation of a restriction site. Therefore it is possible that a single nucleotide polymorphism might also present itself as a restriction, fragment length polymorphism.

SNPs can occur in both coding (gene) and non-coding regions of the genome, including regulatory regions of genes. Many SNPs have no effect on cell function, but can predispose subjects to disease or influence their response to a drug.

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences).

The terms "haplotype" and "SNP-based haplotype" are interchangeably used herein to describe a combination of polymorphisms (SNPs) occurring within a locus on a single chromosome (of either maternal or paternal origin). The "locus" includes the entire coding sequence. A haplotype may be used for detecting complex traits as it contains more than a single SNP. Each haplotype is a set of alleles within families and consideration of multiple closely-linked marker loci can provide a larger number of alleles than provided by usually bi-allelic single SNPs and may demonstrate association with a phenotype more effectively than the component single SNPs. A method for haplotyping is disclosed, for example, in U.S. Pat. No. 6,844,154.

The terms "trait" and "phenotype" are used interchangeably herein and refer to any visible, detectable or otherwise measurable property of an organism such as resistance to or the susceptibility to a disease or a disorder, specifically the susceptibility or resistance to development or aggravation of EPS during treatment with antipsychotic drugs.

The term "haplotype tagging SNPs" also termed hereinafter htSNPs, is used to describe markers being a subset of the markers composing the group of linkage disequilibrium and haplotype diversity within a genomic region. In fact, htSNPs markers capture most of the haplotypes in a region of linkage disequilibrium. Thus, determination of htSNPs enables to retain much of the information of haplotypes by retaining only a reduced subset of markers, thereby saving on resources.

As used interchangeably herein, the term "oligonucleotides", and "polynucleotides" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. The term "nucleotide" is also used herein to encompass "modified nucleotide" which comprise at least one modification, including, for example, analogous linking groups, purine, pyrimidines, and sugars. However, the polynucleotides of the invention are preferably comprised of greater than 50% conventional deoxyribose nucleotides, and most preferably greater than 90% conventional deoxyribose nucleotides The polynucleotide sequences of the invention may be prepared by any known method, including synthetic, recombinant, ex vivo generation, or a combination thereof, as well as utilizing any purification methods known in the art.

The term "linkage disequilibrium", or LD, is the non-random association of alleles at two or more loci. It is not the same as linkage, which describes the association of two or more loci on a chromosome with random recombination between them. LD describes a situation in which some combinations of alleles or genetic markers occur more or less frequently in a population than would be expected from a random formation of haplotypes from alleles based on their frequencies. Linkage disequilibrium is typically caused by fitness interactions between genes or by such non-adaptive processes as population structure, inbreeding, and stochastic effects. In population genetics, linkage disequilibrium is said to characterize the haplotype distribution at two or more loci.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide sequence carried by an individual at a polymorphic marker.

The terms "antipsychotic(s)", "typical antipsychotic(s)" and "conventional antipsychotic(s)" are interchangeably used herein to describe the first generation of antipsychotic medications used to treat psychosis (in particular, schizophrenia). Typical antipsychotics may also be used for the treatment of acute mania, agitation, and other conditions. Typical antipsychotics include haloperidol, penfluridol, sulpiride, zuclopenthixol, flupenthixol, clotiapine and phenothiazines, such as chlorpromazine, prochlorperazine, flupenazine, trifluoperazine, perphenazine, levomepromazine and thioridazine. These drugs cause serious side effects, the most common of which are extrapyramidal symptoms (EPS), particularly, dystonia (abnormal tonicity of the muscles), Parkinsonism and akathisia (motor restlessness), therefore antipsychotics are generally being replaced by atypical antipsychotic drugs.

The term "atypical antipsychotics" as used herein refers to a class of medications used to treat psychiatric conditions with more favorable side effect profile than typical antipsychotics with regard to induction of extrapyramidal symptoms. Due to the decreased propensity of atypical antipsychotics to cause extrapyramidal side effects and an absence of sustained prolactin elevation, atypical antipsychotics are now considered to be first line treatments for schizophrenia and are gradually replacing the typical antipsychotics. Atypical antipsychotics include, but are not limited to: Olanzapine, disclosed in U.S. Pat. No. 5,229,382; Clozapine, disclosed in U.S. Pat. No. 3,539,573; Risperidone, disclosed in U.S. Pat. No. 4,804,663; Sertindole, disclosed in U.S. Pat. Nos. 4,710,500; 5,112,838 and 5,238,945; Quetiapine, disclosed in U.S. Pat. No. 4,879,288; and Ziprasidone, typically administered as the hydrochloride monohydrate. Ziprasidone is disclosed in U.S. Pat. Nos. 4,831,031 and 5,312,925. Its utility in the treatment of schizophrenia is described in U.S. Pat. No. 4,831,031. Aripiprazole and a pharmaceutical solution comprising same are disclosed in U.S. Pat. Nos. 5,006,528 and 6,977,257, respectively.

PREFERRED MODES FOR CARRYING OUT THE INVENTION

The present invention is directed to methods for predicting the susceptibility or resistance of individuals to develop EPS during treatment with antipsychotic drugs. There is considerable variability in the susceptibility of individuals to EPS induced by antipsychotic drugs. For example, acute dystonic reactions are 15 times more common in the young than in the elderly and the risk is higher in those with a previous history or family history of dystonia. The pathophysiology of EPS induced by antipsychotic drugs is still unclear. However, the most influential explanation relates to dopamine D2 receptor blockade. The present invention focuses on the role of dopamine receptor mediated intracellular signaling pathways in early response to typical antipsychotic drugs and in sensitivity to EPS induced by them. The activity of intracellular dopamine is mediated by two major classes of heterotrimeric G protein coupled receptors (GPCR). Receptors of the D1-like class (D1 and D5) are mostly coupled to G-alpha-s/olf, and up-regulate the production of the second messenger cAMP and the activity of its main neuronal target, protein kinase A (PICA). Receptors of the D2-like class (D2, D3 and D4) couple to G-alpha-i/o and down-regulate cAMP production and PICA activity, as well as modulating intracellular calcium levels (Beaulieu et al., Cell, 2005; 122:261-73). Activated receptors trigger G-alpha subunits to exchange GTP for GDP, resulting in the dissociation of the G-alpha subunit from the beta-gamma heterodimers and the subsequent activation of downstream effectors. Heterotrimeric G-proteins behave as molecular switches, and once the G-alpha subunit hydrolyzes GTP to GDP, the hetrotrimer re-forms, thereby terminating signaling. The intensity and duration of signaling by GPCRs are regulated by the regulators of G-protein signaling (RGS) proteins, which accelerate the intrinsic GTPase activity of the G-alpha subunits and reduce the duration of G-protein activation (Ingi et al, ibid). Substantial pieces of evidence indicate that genetic variation in the enzymes responsible for the metabolism of antipsychotic drugs influences the clinical effects of these agents (Kirchheiner et al, 2004; 9:442-73).

RGS and RGS-like proteins are a family of more than 30 members, defined by a common RGS domain, responsible for G-alpha binding, stimulating GTPase activity and termination of downstream signals (Hollinger and Hepler, ibid). Thus, RGS serve as GTPase accelerating proteins (also termed herein GAP). RGS proteins differ widely in their overall size, and many family members possess a remarkable variety of structural domains and motifs, regulating their roles and interactions. Mammalian RGS proteins are grouped into five subfamilies, based on structural and genetic similarities. RGS proteins affect neuronal function and behavior. Most studies have concentrated on worms and mice, and related RGS proteins to behavioral responses, development of the central nervous system (CNS) and anxiety.

In animal models, RGS protein expression is influenced by administration of antipsychotic drugs. mRNA encoded by all five RGS genes tested in the current study is down regulated after chronic exposure to risperidone (Geurts et al., Biochem Pharmacol., 2003; 66:1163-70). RGS2 influences the D1 receptor pathway and dopamine receptors agonists and antagonists may regulate the expression of RGS2 and RGS4 (Taymans et al., Eur J Neurosci., 2004; 19:2249-60). RGS9 over-expression or knockout in rat nucleus-accumbens affects responses to cocaine and some dopamine agonists. RGS9 knockout mice develop dyskinesias associated with dopamine pathways, when inhibition of dopaminergic transmission by haloperidol is followed by activation of D2 receptors (Kovoor et al., J Neurosci., 2005; 25:2157-65).

In the human context, some of the RGS genes have been shown to be expressed in brain, (Larminie et al., Brain Res Mol Brain Res. 2004; 17:24-34). They include RGS2, RGS4, RGS8, RGS9 and RGS10. RGS4 is a promising candidate gene for schizophrenia (Chowdari et al., Hum Mol Genet.

2002; 11:1373-1380), but the findings of association studies in different ethnic groups are inconsistent. The inventors of the present invention discovered that of five RGS protein encoding genes, genetically based variation in RGS2 gene influence the tendency to develop EPA during treatment with typical antipsychotic drugs.

RGS2 is a small gene (3,235 bp). As depicted in FIG. 1, only two of the 5 SNPs that were studied are located within the gene (rs2746073 is intronic and rs4606 is in the 3' UTR). Two SNPs are upstream the RGS2 locus (rs1933695 and rs2179652) and two downstream (rs1819741 and rs1152746), all within the 20,000 bp flanking region. Two 5-SNP haplotypes (RGS2-HAP$^+$ and RGS2-HAP), were found to be associated with worsening of or resistance, respectively to EPS during treatment with typical antipsychotic drugs. Without wishing to be bound by any particular theory or mechanism of action this association may be attributed to a consequence of linkage disequilibrium between the five SNPs (i.e. rs2746073, rs1933695, rs2179652, rs1819741 and rs1152746) and as yet unidentified variants that influence structure and/or function and are located in the coding or regulatory regions of the gene.

It is to be understood explicitly that the scope of the present invention encompasses any SNP within the RGS2 gene or within regions flanking the RGS gene, with the stipulation that this SNP correlates with worsening of or resistance to EPS induced by antipsychotic drugs. Thus, the SNPs of the invention may reside in coding sequences, intronic regions, or in regions of an unknown function. If located in a coding region, the polymorphism can result in an amino acid alteration. Such alteration may or may not have an effect on the function or activity of the encoded polypeptide. A polymorphism located in a non-coding region may cause alternative splicing, which again, may or may not have an effect on the encoded protein activity or function. Particularly, polymorphism in the RGS2 according to the present invention encompasses single nucleotide polymorphisms, biallelic and otherwise as exemplified in Tables 3A, 6A and 7A.

It should be further understood that diagnosing resistance to EPS or predisposition to EPS by detecting variant mRNAs or gene product(s) are also encompassed within the scope of the present invention. As used herein a "variant mRNA" or a "variant gene product" refer to a mRNA or a gene product, respectively, which are spliced or encoded by the variant allele comprising at least one polymorphic site according to the present invention, including, but not limited to, a full length mRNA or gene product, an essentially full-length mRNA or gene product and a biologically active fragment of the gene product. Biologically active fragments include any portion of the full-length polypeptide which confers a biological function on the variant gene product, including ligand binding and antibody binding. Ligand binding includes binding by nucleic acids, proteins or polypeptides, small biologically active molecules, or large cellular structures.

A variant gene product is also intended to mean gene products which have altered expression levels or expression patterns which are caused, for example, by the variant allele of regulatory sequence(s).

The RGS2 protein consists of 211 amino acids and belongs to the B/R4 subfamily of RGS proteins (which also includes RGS1-5, RGS8, RGS13, RGS16 and RGS18). All members are structurally simple, and do not have other identifiable features besides their RGS domain, which mediates the GAP activity and its interaction with G-alpha subunits (Hollinger and Hepler, ibid). This domain is composed of nine alpha helices that fold into two small sub-domains. The 78 amino acids N-terminal region of the RGS2 protein has a role in plasma membrane targeting. Functionally, RGS2 blocks Gq-alpha mediated signaling, a finding consistent with its potent Gq-alpha GAP activity (Kehrl and Sinnarajah, Int J Biochem Cell Biol., 2002, 34:432-8). Among G protein coupled receptors whose signaling is reported to be influenced by RGS2 are the dopamine D1 receptor (Taymans et al., J Neurochem., 2003, 84:1118-27) the 5-HT2A receptor (Ghavami et al., Cell Signal 2004, 16:711-21) and the M1 muscarinic, cholinergic receptor (Bernstein et al, J. Biol. Chem., 2004, 279:21248-56). RGS2 has no effect on the signaling mediated by the G-alpha i/o coupled 5-HT1A and the dopamine D2 receptors (Ghavami et al., ibid) the major target of the antipsychotics drugs. On the other hand, dopamine receptors themselves may regulate the expression of RGS2. D1R agonist or D2R antagonist up-regulate RGS2 mRNA in the rat striatum, while a D1R antagonist or a D2R agonist cause a down-regulation of RGS2 (Taymans, 2003, ibid).

A person skilled in the art of psychiatry will find the present invention useful for planning an adequate treatment regimen for treating psychosis. It is known in the art that one of the most undesired and common side-effect of antipsychotic treatments is EPS. EPS induced by antipsychotics evolve even when the drugs fail to provide adequate relief. It is further known that the current psychiatric practice offers a variety of antipsychotic treatments and criteria for choosing the therapeutic regimen. However, to date, susceptibility to induction or enhancement of EPS cannot be assessed and therefore is not a valid criterion for selecting a treatment regimen. The need to determine susceptibility to EPS induced by antipsychotics is crucial since EPS often lead patients to stop using the medications. Moreover, EPS seriously damages patient's functioning and wellbeing.

In recent years, genetic alterations, also termed DNA polymorphisms or markers including SNPs or combinations thereof, i.e. haplotypes, which cause or contribute to various diseases have been identified. Use of SNPs and haplotypes for identifying the likelihood to develop a particular disease was previously exemplified. For example, particular haplotypes within the BRCA1 gene, which indicate susceptibility to the pathology associated with breast, ovarian, prostate and other cancers are disclosed in U.S. Pat. No. 6,951,721. In another example, in one of the genes associated with Alzheimer's disease, apolipoprotein E or ApoE, SNPs affect disease development. This gene contains two SNPs that result in three possible alleles for this gene: E2, E3, and E4. Each allele differs by one DNA base, and the protein product of each gene differs by one amino acid. Each individual inherits one maternal copy of ApoE and one paternal copy of ApoE. Research has shown that an individual who inherits at least one E4 allele will have a greater chance of getting Alzheimer's disease. Apparently, the change of one amino acid in the E4 protein alters its structure and function enough to make disease development more likely. Inheriting the E2 allele, on the other hand, seems to indicate a tendency for a late onset of the disease, therefore, recognizing same can be used to search for and isolate the disease-causing gene.

The present invention now discloses SNPs and haplotypes associated with resistance or susceptibility to EPS induced by antipsychotic drugs, using extensive genotyping research. To create a genetic test that will screen for SNPs and haplotypes correlated with treatment induced EPS, blood samples were collected from a group of individuals in an acute psychotic state. The DNA of RGS genes was analyzed for the presence of SNPs and their association with EPS, such as Parkinsonism and akathisia. Eventually, the association of SNPs and haplotypes within RGS2 with susceptibility or with resistance to treatment-induced EPS was established as demonstrated in Tables 3A-B, 4, 5, 6A-B and 7A-B.

It is to be understood that "resistance" or "susceptibility" to EPS induced by antipsychotic drugs do not necessarily mean that the subject will be resistant to EPS or will develop EPS, upon treatment with antipsychotic drugs but rather that the subject is, in a statistical sense, more likely to be resistant to EPS or to develop EPS than an average member of the population. As used herein, "resistance" or "susceptibility" to EPS induced by antipsychotic drugs may exist if the subject has one or more genetic determinants (e.g., polymorphic variants or alleles) that may, either alone or in combination with one or more other genetic determinants, contribute to an increased resistance to EPS or an increased risk of developing EPS in some or all subjects. Ascertaining whether a subject has any such genetic determinants according to the teaching of the present invention is useful, for example, for purposes of genetic counseling and for diagnostics tests before determining the treatment regimen of psychotic patients.

DNA analyzed herein for determining the presence of SNPs within RGS2 gene or fragments thereof in a subject treated with antipsychotic drugs, may be extracted from virtually any body sample, such as blood (other than pure red blood cells), tissue material and the like by a variety of techniques such as that described by Maniatis, et. al. (Molecular Cloning: A Laboratory Manual, Cold Spring Harbor, N.Y., pp. 280-281, 1982). Convenient tissue samples include whole blood, semen, saliva, tears, urine, fecal material, sweat, buccal material, skin and hair. For assay of cDNA or mRNA, the tissue sample must be obtained from an organ in which the target nucleic acid is expressed. According to certain embodiments, the genomic DNA sample is obtained from whole blood samples or EBV-transformed lymphoblast lines. The sample can be obtained from any suitable subject, i.e. an adult, child, fetus, or embryo. According to certain embodiments of the invention the sample is obtained prenatally, either from the fetus or embryo or from the mother (e.g., from fetal or embryonic cells that enter the maternal circulation).

Typically, the sample obtained from the subject is processed before the detecting step, e.g. the DNA in the cell or tissue is separated from other components of the sample, and the target DNA is amplified as described herein below. All samples obtained from a subject, including those subjected to any sort of further processing, are considered to be obtained from the subject.

If the extracted sample is impure, it may be treated before analysis with an amount of a reagent effective to open the cell membranes of the sample, and to expose and/or separate the strand(s) of the nucleic acid(s). This lysing and nucleic acid denaturing step exposes and separates the strands.

Preferably, the DNA sequences of the RGS2 gene and fragments thereof determined according to the methods of the invention encompasses SNPs as set forth by SEQ ID NOS. 1-6 (Table 3A), or haplotypes as set forth in Tables 5, 6A-B and 7A-B.

The DNA obtained from a subject, for determining the presence of polymorphisms in the RGS2 gene is typically amplified. The deoxyribonucleotide triphosphates dATP, dCTP, dGTP, and dTTP are added to the synthesis mixture, either separately or together with the primers, in adequate amounts and the resulting solution is heated. After the heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature. The primers used to amplify the strands corresponding to RGS2 gene or fragments thereof are oligonucleotides of sufficient length and appropriate sequence to provide initiation of polymerization. Environmental conditions conducive to synthesis include the presence of nucleoside triphosphates and an agent for polymerization, such as DNA polymerase, and a suitable temperature and pH. Each primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12-20 or more nucleotides, although it may contain fewer nucleotides.

The term "primer" refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

Primers used to carry out this invention are designed to be substantially complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the mutation to hybridize therewith and permit amplification of the genomic locus.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al., (Tetrahedron Letters, 1981; 22:1859-1862). Alternatively, the primers of the invention may be synthesized on a modified solid support as described in U.S. Pat. No. 4,458,066.

The agent for polymerization may be any compound or system which will function to accomplish the synthesis of primer extension products, including enzymes. Suitable enzymes for this purpose include, for example, E. coli DNA polymerase I, Klenow fragment of E. coli DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the process. In the next step, the newly synthesized double-stranded molecule is subjected to denaturing conditions using any of the procedures described above to provide single-stranded molecules. The steps of denaturing, annealing, and extension product synthesis can be repeated as often as needed to amplify the target polymorphic locus nucleic acid sequence to the extent necessary for detection. The amount of the specific nucleic acid sequence produced will accumulate in an exponential fashion. Amplification is described in PCR—A Practical Approach, ILR Press, Eds. McPherson, Quirke and Taylor, 1992.

Although the method of amplifying is preferably PCR, as described herein and as is commonly used by those of ordinary skill in the art, alternative methods of amplification can also be employed as long as the genetic locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to $10^8$ copies within 60 to 90 minutes. Alternatively, nucleic acid can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is $10^8$ to $10^9$ fold. Another amplification system useful in the method of the invention is the QB Replicase System. The QB replicase system can be utilized by attaching an RNA sequence called MDV-1 to RNA complementary to a DNA sequence of interest. Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking DNA repair. Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. Hindi is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than $10^7$-fold amplification in 2 hours at 37° C. Unlike PCR and LCR, SDA does not require instrumented temperature cycling. Another method is a process for amplifying nucleic acid sequences from a DNA or RNA template which may be purified or may exist in a mixture of nucleic acids. The resulting nucleic acid sequences may be exact copies of the template, or may be modified. The process has advantages over PCR in that it increases the fidelity of copying a specific nucleic acid sequence, and it allows one to more efficiently detect a particular point mutation in a single assay. A target nucleic acid is amplified enzymatically while avoiding strand displacement. Three primers are used. A first primer is complementary to the first end of the target. A second primer is complementary to the second end of the target. A third primer which is similar to the first end of the target and which is substantially complementary to at least a portion of the first primer such that when the third primer is hybridized to the first primer, the position of the third primer complementary to the base at the 5' end of the first primer contains a modification which substantially avoids strand displacement. This method is detailed in U.S. Pat. No. 5,593,840. Although PCR is the preferred method of amplification if the invention, these other methods can also be used to amplify the gene of interest.

The amplification products may be detected by Southern blots analysis, without using radioactive probes. In such a process, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 1985; 3:1008-1012), allele-specific oligonucleotide (ASO) probe analysis (Conner, et al., Proc. Natl. Acad. Sci. U.S.A., 1983; 80:278), oligonucleotide ligation assays (OLAs; Landgren, et al., 1988; Science, 241:1007), heteroduplex analysis, chromatographic separation and the like. Molecular techniques for DNA analysis have been reviewed (Landgren, et al., Science, 1988; 242:229-237).

A number of methods well known in the art can be used to carry out the sequencing reactions. Commonly, enzymatic sequencing based on the Sanger dideoxy method is used as described, for example, in Sanger et al., Proc. Natl. Acad. Sci. 1977; 74:5463. Mass spectroscopy may also be used. Well known sequencing methods also include Maxam-Gilbert chemical degradation of DNA (see Maxam and Gilbert, Methods Enzymol., 1980; 65:499). One skilled in the art recognizes that sequencing is now often performed with the aid of automated methods.

The sequencing reactions can be analyzed using methods well known in the art, such as polyacrylamide gel electrophoresis. In a preferred embodiment for efficiently processing multiple samples, the sequencing reactions are carried out and analyzed using a fluorescent automated sequencing system such as the Applied Biosystems, Inc. ("ABI", Foster City, Calif.) system. For example, PCR products serving as templates are fluorescently labeled using the Taq Dye Terminator Kit (Perkin-Elmer). Dideoxy DNA sequencing is performed in both forward and reverse directions on an ABI automated Model 377™ sequencer. The resulting data can be analyzed using "Sequence Navigator™" software available through ABI. Alternatively, large numbers of samples can be prepared for and analyzed by capillary electrophoresis, as described, for example, in U.S. Pat. No. 5,498,324.

Determining the presence and identity of SNPs or haplotypes which correlate with onset or increase in EPS during treatment with antipsychotic drugs may be carried out by any one of the various tools for the detection of polymorphism on a target DNA known in the art, including, but not limited to, allele-specific probes, allele specific primers, direct sequencing, denaturing gradient gel electrophoresis and single-strand conformation polymorphism. Preferred techniques for SNP genotyping should allow large scale automated analysis, which do not require extensive optimization for each SNP analyzed.

The phrase "identifying a polymorphism" or "identifying a polymorphic variant" as used herein generally refers to determining which of two or more polymorphic variants exists at a polymorphic site. In general, for a given polymorphism, any individual will exhibit either one or two possible variants at the polymorphic site (one on each chromosome). This may, however, not be the case if the individual exhibits one more chromosomal abnormality such as deletions.

Oligonucleotides that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site within it or at least at one end) will generally hybridize preferentially to a nucleic acid comprising that sequence as opposed to a nucleic acid comprising an alternate polymorphic variant.

The design and use of allele-specific probes for analyzing polymorphisms is described, for example, in U.S. Pat. No. 5,348,855 and International Application WO89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Typically, a probe comprises a region of nucleotide sequence that hybridizes to at least about 8, preferably to about 10 to 15, more preferably to about 20-25 and most preferably to about 40-75 consecutive nucleotides of a nucleic acid molecule. Preferably, the probes are designed as to be sufficiently specific to be able to discriminate the targeted sequence for only one nucleotide variation. According to certain embodiments, the probes are labeled or immobilized on a solid support by any suitable method as is known to a person skilled in the art. The probes can be used in Southern hybridization to genomic DNA or Northern hybridization to mRNA; the probes can also be used to detect PCR amplification products. By assaying the hybridization to an allele specific probe, one can detect the presence or absence of a polymorphism in a given sample. Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence. High-Throughput parallel hybridizations in array format are particularly preferred to enable simultaneous analysis of a large number of samples.

Alternative method for the detection and identification of polymorphism on a target DNA utilizes allele-specific primers, as described herein above. The direct analysis of the sequence of polymorphisms of the present invention can be accomplished using either the dideoxy chain termination method or the Maxam Gilbert method (see Sambrook et al., Molecular Cloning, A Laboratory Manual (2nd Ed., CSHP, New York 1989); Zyskind et al., Recombinant DNA Laboratory Manual, (Acad. Press, 1988). It should be recognized that the field of DNA sequencing has advanced considerably in the past several years, specifically in reliable methods of automated DNA sequencing and analysis. These advances and those to come are explicitly encompassed within the scope of the present invention. As is known to a person skilled in the art, an amplified product can be sequenced directly or subcloned into a vector prior to sequence analysis.

Alleles of target sequences can be differentiated using single-strand conformation polymorphism analysis, which identifies base differences by alteration in electrophoretic migration of single stranded PCR products. Amplified PCR products can be generated as described above, and heated or otherwise denatured, to form single stranded amplification products. Single-stranded nucleic acids may refold or form secondary structures which are partially dependent on the base sequence. The different electrophoretic mobility of single-stranded amplification products can be related to base-sequence difference between alleles of target sequences.

Another method for rapid and efficient SNP analysis makes use of thermal denaturation differences due to differences in DNA base composition. In one embodiment of this test, allele specific primers are designed as above to detect biallelic SNP with the exception that a 5' GC tail of 26 bases is added to one primer. After PCR amplification with a single, common reverse primer, a fluorescent dye that binds preferentially to dsDNA (e.g., SYBR Green 1) is added to the tube and then the thermal denaturation profile of the dsDNA product of PCR amplification is determined. Samples homozygous for the SNP amplified by the GC tailed primer will denature at the high end of the temperature scale, while samples homozygous for the SN amplified by the non-GC tagged primer will denature at the low end of the temperature scale. Heterozygous samples will show two peaks in the thermal denaturation profile.

The invention further contemplates modifications of the methods described above, including, but not limited to allele-specific hybridization on filters, allele-specific PCR, fluorescence allele-specific PCR, PCR plus restriction enzyme digest (RFLP-PCR), denaturing capillary electrophoresis, dynamic allele-specific hybridization (DASH), 5' nuclease (Taq-Man™) assay, and the primer extension and time-of-flight mass spectrometry. According to certain currently preferred embodiments, the polymorphism of the present invention is detected using the primer extension and time-of-flight mass spectrometry method as exemplified herein below.

EXAMPLES

Clinical Methods

Israel Study Sample

The study sample consisted of inpatients with schizophrenia (as defined by DSM-IV) admitted to the Beer Yaakov Mental Health Center (a large state referral facility) in an acute psychotic state. Subjects were between the ages of 18-65 years, male or female, Jewish, with information regarding Ashkenazi or non-Ashkenazi origin recorded. Diagnoses were established by the Structured Clinical Interview for DSM-IV Axis I, Patient Edition by two board certified psychiatrists. Patients with evidence of neurological or medical conditions that could impact upon the outcome of antipsychotic treatment or be associated with a propensity to develop adverse effects were excluded from study participation. Patients with a history of substance or alcohol dependence or abuse were excluded. All subjects provided written informed consent after receiving a full explanation regarding the nature of the study and potential risks and benefits of participation. A psychiatrist independent of the study documented decisional capacity. The Beer Yaakov Mental Health Center Institutional Review Board and the Ministry of Health Ethical Review Board approved the study.

The design of the study was naturalistic. Only patients whose treating physicians prescribed typical antipsychotics, alone or in combination with the atypical antipsychotic-risperidone, were included. A blood sample (30 ml.) was obtained and transferred to the laboratory for DNA extraction. Clinical ratings were performed at baseline and again after 2 weeks, provided that the patient continued to receive the same antipsychotic drugs during this period, although not necessarily at the same dose. All the patients were rated by the same clinician. Clinical outcome was rated with the Positive and Negative Symptoms Scale (PANSS; Kay et al, Schizophr. Bull., 1987; 13:261-76). Extrapyramidal effects were evaluated with the Simpson Angus Scale, the Barnes Akathisia Scale and the Abnormal Involuntary Movements Scale (AIMS; Guy, ECDEU assessment Manual for Psychopharmacology, US Dept Health, Education, and Welfare publication (ADM) 76-338, Rockville Md.: National Institute of Mental Health, 1976).

The study sample consisted of 121 patients, 72 of whom were treated with typical antipsychotic drugs (TYP) and 49 of whom were treated with typical antipsychotics+risperidone (TYP-R). The typical antipsychotics administered were: zuclopenthixol (52.4%), haloperidol (20.2%), perphenazine (11.5%), clotiapine (10.6%), fluphenazine (8.7%), flupenthixol (2.9%), levomepromazine (2.4%), chlorpromazine (1.0%), sulpiride (1.0%), penfluridol (1.0%). Patients treated with both TYP and TYP-R showed a significant improvement from baseline to the two week time point on PANSS total score (F [treatment effect]=89.9, df [1, 119]) p<0.0000001). Percent change in PANSS total score from baseline to two weeks was 12.1±15.4% for all the patients, 12.0±11.6% for the TYP patients and 12.3±19.7% for the TYP-R patients. There was also no significant difference in Simpson Angus, Barnes Akathisia and AIMS change scores over two weeks of treatment between patients treated with TYP or TYP-R.

U.S. Study Sample

Details of the sample and study design are described in a previous publication (Smith et al, Int J Neuropsychopharmacology, 2005; 8:183-194.). In brief, this was a cross-sectional study of patients with schizophrenia or schizoaffective disorder diagnosed according to DSM-IV criteria, who had been treated with a single antipsychotic agent (clozapine, olanzapine, risperidone or a first generation antipsychotic) for at least a month and were hospitalized at one of three tertiary care public hospitals in the United States. Patients gave written informed consent for participation in the study, after the purposes and procedures were explained. The protocol and consent forms were approved by the Internal Review Board of each institution. Recruitment was consecutive and sampling procedures were continued until there were approximately 50 patients in each of the 4 groups. Clinical state was evaluated by the Positive and Negative Symptoms Scale (PANSS) as described for the Israel study sample hereinabove. The scales were administered on two separate occasions, separated by at least a week, by the same clinician. The mean score of the two assessments was used for data analysis. For DNA extraction, 30 cc of blood were collected in EDTA tubes. In addition, the patients were evaluated for fasting glucose and lipids; the results of these assays and their relationship to antipsychotic treatment are reported in Smith et al (2005, ibid).

The sample for the current study (clinical ratings and DNA available) consisted of 184 patients of African-American (AA, n=112), Hispanic (n=41) or white (n=27) ethnic origin. Hispanics and whites were combined as a single Caucasian group (n=68). Distribution among the antipsychotic treatment groups was as follows: typical antipsychotic drugs (n=44), risperidone (n=46), olanzapine (n=49) and clozapine (n=41). No significant difference was seen in mean SAS scores among patients in the different antipsychotic groups.

Genotyping

Israel Study Sample

The focus of this work was on 5 RGS genes: RGS2, RGS4, RGS8, RGS9 and RGS10. The SNPs used in the study were selected based on three different databases: dbSNP, Ensembl Genome Browser and Sequenom RealSNP. We selected SNPs that fulfilled the following criteria: (1) located within the gene of interest or no more then 20,000 bases upstream or downstream; (2) reported heterozygosity >0.1. The heterozygosity of the selected SNPs was checked by genotyping 24 Jewish Israeli control subjects and was found appropriate. Altogether 26 SNPs fulfilled these conditions, without significant differences between Ashkenazi and non-Ashkenazi subjects. SNPs that showed significant deviation from HWE (n=2) were excluded from further analysis. A list of the 24 SNPs that were included in the analysis, with details of their location and minor allele frequency (MAF) in this sample, is provided in Table 3A.

SNP genotyping was performed with a high-throughput system of chip-based mass spectrometry (matrix-assisted laser desorption/ionization time-of-flight; MALDI-TOF) (Sequenom, San Diego, Calif.). The allele determination in the sampled DNA was based on MALDI-TOF mass spectrometry of allele-specific primer products (Little et al., J Mol Medicine 1997a; 75:745-750; (Little et al., Eur J Clin Chem Clin Biochem., 1997b; 35:545-548). Genotyping assays were designed as multiplex reactions using SpectroDESIGNER software version 2.0.7 (Sequenom). Primers were synthesized by Integrated DNA Technologies (Coralville, Iowa). Optional primers that can be used for carrying out the methods of the invention are listed in Table 1 hereinbelow. The detailed PCR and primer extension reactions were according to the protocol for high multiplex homogeneous MassEXTEND (hME) procedure (Sequenom application notes, and described in McCullough et al., Nucleic Acids Res., 2005; 33: e99).

TABLE 1

Exemplary primers for detecting the SNPs of the invention

| Polymorphism Nucleotide No. (SNP database No.) | Primer | Primer's sequence | SEQ ID NO: |
|---|---|---|---|
| 189496477 (rs1933695) | 1-PCR | ACGTTGGATGCAGTATACAGATCACACCTG | 7 |
|  | 2-PRC | ACGTTGGATGCGCTCAACTGTTGAAGTTCC | 8 |
|  | UEP_SEQ | TTCTGCAGATTTACTATCCACT | 9 |
| 189501483 (rs2179652) | 1-PCR | ACGTTGGATGTGAGCTCTTGGTGGAATCTG | 10 |
|  | 2-PRC | ACGTTGGATGCTGTAGATTCTAGCCTTGGG | 11 |
|  | UEP_SEQ | CCTTTCATAGTCCAGCCCTG | 12 |
| 189510884 (rs2746073) | 1-PCR | ACGTTGGATGGCAACACTTGAATATGCTAC | 13 |
|  | 2-PRC | ACGTTGGATGTGCCTTATGCGGTTTGTCTC | 14 |
|  | UEP_SEQ | TGGGTGACTTTATTTGGTAAAAA | 15 |
| 189512829 (rs4606) | 1-PCR | ACGTTGGATGAGTACTGATGATCTGTGGTC | 16 |
|  | 2-PRC | ACGTTGGATGGGATTCAGTAACAGTGAAGTG | 17 |
|  | UEP_SEQ | AGTGAAGTGTTTACTATGTGCAA | 18 |
| 189516495 (rs1819741) | 1-PCR | ACGTTGGATGAGCAATCATAGCTCACACTC | 19 |
|  | 2-PRC | ACGTTGGATGCCTATCCTCCAAGAAGTACC | 20 |
|  | UEP_SEQ | AATTAAGTAGCTGATGAAATAAATA | 21 |
| 189528562 (rs1152746) | 1-PCR | ACGTTGGATGAGCATTCCTGATATCAGCAC | 22 |
|  | 2-PRC | ACGTTGGATGGCACAGTGCATACAAAACAC | 23 |
|  | UEP_SEQ | GTTAAGAGGAAATTCTGTGGCA | 24 |

The high-throughput liquid handling was performed with the aid of a MULTIMEK 96 automated 96-channel robot (Beckman Coulter, Fullerton, Calif.). Primer extension products were loaded onto a 384-element chip (SpectroCHIP; Sequenom) by nanoliter pipetting robot (SpectroPOINT, Sequenom) and analyzed with a MassARRAY mass spectrometer (Bruker Daltonik, Bremen, Germany). The resulting mass spectra were processed and analyzed for peak identification and allele determination with the MassARRAY TYPER version 3.1.4.0 software (Sequenom). About 10% of the total calls were given a low score by the Sequenom caller software, and were inspected manually for the correct call.

U.S. Study Sample

Genomic DNA was extracted from whole blood using the Puregene® DNA purification system (Gentra Systems MA, USA). The six SNPs within or flanking the RGS2 gene (upstream and downstream) identified in the Israel sample as described herein were genotyped: rs1933695, rs2179652, rs2746073, rs4606, rs1819741 and rs1152746. (Greenbaum et al, Pharmacogenetics and Genomics, 2007; In Press). Two SNPs that showed a statistically significant (P<0.05) allele frequency difference between AA and Caucasians, and were excluded from the analysis of the overall sample (rs1933695 and rs2746073). No SNPs showed significant deviation from Hardy-Weinberg equilibrium (HWE).

SNP genotyping was performed using the TaqMan Assay-On-Demand™, purchased from Applied Biosystems (Foster City, Calif., USA). The assay contains two primers and two MGB-TaqMan probes. The PCR reaction was performed according to the manufacturer's instructions. In short, 10-30 ng of gDNA were added to a reaction mixture containing 0.22 µl 20× assay reagent and 2.5 µl 2× TaqMan Universal PCR Master Mix (Applied Biosystems) in a total volume of 5 µl in 384-wells plate. PCR conditions were 2 min at 50°, 10 min at 90° and 45 cycles of 15 sec at 95° and 1 min at 60°. Real-Time PCR was performed and analyzed in an ABI PRISM 7900 HT Sequence Detection System (Applied Biosystems) with the SDS 2.3 software. For the purpose of quality control, ~10% of the samples were genotyped twice; the match rate was 99%.

Statistical Analysis

Israel Study Sample

Ratings of clinical state and adverse effects were analyzed at baseline and after two weeks for patients whose treatment regimen during this time consisted of typical antipsychotics (TYP) or typical antipsychotics plus risperidone (TYP-R). SPSS version 12.01 was used to perform Student t tests, chi square tests or analysis of variance (ANOVA). The primary outcome variable for clinical response was the PANSS change score calculated by subtracting the score at two weeks from the score at baseline. For categorical analyses patients with change scores above the median were grouped as early responders (ER) and patients with scores at or below the median as non-early responders (N-ER). The primary outcomes variable for extrapyramidal symptoms of the Parkinson type was the SAS change score calculated by subtracting the score at two weeks from the score at baseline. For categorical analyses, patients demonstrating worsening of existing Parkinson symptoms during treatment or patients without parkinsonism at admission who developed it during the two weeks antipsychotic treatment were grouped as PARK+ (n=33). Patients showing improvement of existing Parkinson symptoms during treatment or patients without parkinsonism at admission and after the two weeks of antipsychotic treatment were grouped as PARK– (n=82). The same analyses were done for the BAS and AIMS. Twenty-seven patients showed onset or worsening of akathisia after two weeks of treatment with TYP or TYP-R. Only 10 patients showed onset or worsening of abnormal involuntary movements after two weeks of treatment; therefore, no further analyses were performed of results based on the AIMS.

Haploview (version 3.12) was used to examine linkage disequilibrium (LD) between SNPs, to define LD blocks and to detect significant departure from Hardy Weinberg equilibrium (HWE). Haploview was also used to perform single SNP association tests, for haplotype population frequency estimation and to perform haplotype association tests. P values <0.05 (two tailed) were regarded as nominally significant.

Bonferonni correction was applied for the number of tests performed for each phenotype.

We analyzed the power of our sample to detect association of individual SNPs with early response to treatment using Power and Precision V2.0, 2000. The analysis was based on 240 chromosomes divided approximately equally between the ER and N-ER groups. The analysis indicated that the smallest allele frequency difference (effect size) that could be detected with 80% power (alpha 0.05, two tailed) ranged from 0.11 (95% CI: 0.03-0.19) to 0.17 (95% CI: 0.05-0.29). Given the disproportionate division of patients between the PARK+ (n=33) and PARK- groups (n=82), power was lower for this comparison. The smallest allele frequency difference that could be detected with 80% power (alpha 0.05, two tailed) ranged from 0.14 (95% CI: 0.06-0.28) to 0.20 (95% CI: 0.07-0.23). For the Akathisia+/-Akathisia-comparison the smallest allele frequency difference that could be detected with 80% power (alpha 0.05, two tailed) ranged from 0.15 (95% CI: 0.07-0.23) to 0.22 (95% CI: 0.08-0.36).

U.S. Study Sample

For categorical analysis, patients with a SAS score of zero on two evaluations were grouped as null (PARK-) for the phenotype of antipsychotic-induced parkinsonism (AIP) and patients whose average SAS score was above zero were grouped as positive (PARK+). To further explore association of the RGS2 gene with AIP we defined the upper quartile of patients according to SAS scores as PARK75% and compared them to PARK- patients. The same approach was used to analyze the akathisia phenotype according to the BAS. Allele and genotype frequencies were compared in PARK- vs. PARK+ and PARK75% patients and in Akathisia+ and Akathisia- patients by chi-square tests. Haploview (version 3.12) (Broad Institute, Cambridge, Mass., USA) was used to examine linkage disequilibrium (LD) between SNPs, to define LD blocks (according to the confidence interval algorithm of Gabriel [2002]), to detect significant departure from Hardy Weinberg equilibrium (HWE) and to perform haplotype population frequency estimation. Individual haplotypes were extracted from the population genotype data with the program, PHASE V.2. (Stephens et al., Am J Hum Genet., 2001; 68:978-989; Stephens et al., Am J Hum Genet., 2003; 73:1162-1169). Odds ratios and 95% confidence intervals were calculated by logistic regression, taking into account PANSS scores since these were significantly higher among PARK+ compared to PARK- patients as well as age and gender. Ethnicity and drug treatment group did not significantly influence the model and were not included.

Example 1

Demographic and Clinical Features at Baseline and Drug Treatment: Israel Study Sample The first set of genetic associations that we examined was of RGS genes with response to antipsychotic treatment at two weeks. Early responders (ER) at this time point, defined by a change in scores on PANSS that exceeded the median, were compared to non-early responders (N-ER). Patients with treatment emergent or worsening Parkinsonism (PARK+) were compared with patients without treatment emergent or worsening Parkinsonism (PARK-) after two weeks of antipsychotic treatment. ER (N=61) and N-ER (N=60) did not differ in background and demographic features including age, gender, education, age at onset, age at first psychiatric hospitalization, cumulative psychiatric hospitalization, dose of typical antipsychotics and risperidone and other treatment details (Table 2). There was a trend for PANSS total scores to be slightly higher in the ER group (ER=24.5±6.4, N-ER=22.0±7.2; p=0.05). There were no significant differences between the ER and N-ER groups in allele and genotype frequency of the 24 SNPs that were tested in 5 RGS genes except for one SNP in RGS9 (rs1877822) that was nominally significant in the comparison of genotype frequency only (p=0.03).

TABLE 2*

Israel Study Sample: background and demographic features

| Feature | ER | | N-ER | | PARK+ | | PARK- | |
|---|---|---|---|---|---|---|---|---|
| Number | 61 | | 60 | | 33 | | 82 | |
| Age (yrs.) | 37.1 | 12.1 | 39.7 | 13.3 | 36.4 | 11.8 | 38.9 | 12.9 |
| No. of male gender (%) | 38 (65.5) | — | 47 (79.7) | — | 23 (71.9) | — | 58 (74.4) | — |
| Education (yrs.) | 10.8 | 2.7 | 10.3 | 3.2 | 10.3 | 2.9 | 10.6 | 3.0 |
| Age at onset (mean, yrs) | 24.3 | 7.0 | 23.6 | 9.8 | 23.6 | 5.7 | 24.3 | 9.7 |
| Age 1st psychiatric hospitalization (yrs.) | 24.8 | 7.2 | 24.4 | 10.7 | 24.2 | 7.9 | 24.8 | 10.0 |
| Cumulative psychiatric hospitalization (months/years at risk) | 1.2 | 1.1 | 1.4 | 2.0 | 1.6 | 2.6 | 1.1 | 1.1 |
| Typical antipsychotic dose (CPZ units/day) | 426.0 | 412.0 | 435.2 | 234.9 | 414.46 | 481.9 | 433.4 | 339.7 |
| Risperidone dose (mg/day) | 2.9 | 1.1 | 3.3 | 2.0 | 2.75 | 0.9 | 3.2 | 1.5 |
| 2 Typical antipsychotics number (%) | 19 (31.7) | — | 17 (28.3) | — | 13 (39.3) | — | 23 (28.2) | — |
| Concomitant benzodiazepines number (%) | 14 (23.0) | — | 12 (20.0) | — | 9 (27.3) | — | 16 (10.5) | — |
| Concomitant anticholinergics number (%) | 26 (42.7) | — | 23 (38.3) | — | 16 (48.5) | — | 31 (37.8) | — |

*No comparisons, by Pearson chi square or Student t test, were significant at p < 0.1

Example 2

Association of the RGS SNPs With Development of EPS

Results are based on the Israel study sample. Samples from 6 of the 121 patients were not available for these analyses for technical reasons. PARK+ patients. (N=33), who manifested emergent or worsening Parkinson symptoms, as defined by the SAS, were compared to patients without worsening of EPS or treatment emergent symptoms (PARK−, N=82) The two groups did not differ on background or demographic features including age, gender, education, age at onset, age at first psychiatric hospitalization, cumulative psychiatric hospitalization, dose of typical antipsychotics and risperidone and other treatment details (Table 1).

Several SNPs in RGS genes were examined. These SNPs are listed in Table 3A. Baseline SAS scores were similar (PARK+=12.2±3.1, PARK−=13.9±4.7). As shown in Table 3B, five SNPs within or flanking the RGS2 gene were significantly associated with emergence or worsening of Parkinson symptoms over two weeks of treatment with TYP or TYP-R. Nominally significant differences in allele frequency were observed for rs2179652 (SEQ ID NO:2; p=0.006), rs2746073 (SEQ ID NO:3; p=0.0078), rs4606 (SEQ ID NO:4; p=0.0008), rs1819741 (SEQ ID NO:5; p=0.001) and rs1152746 (SEQ ID NO:6; p=0.0455). Two of these differences (rs4606 and rs1819741, corresponding to SEQ ID NOS: 4 and 5, respectively) survived Bonferonni correction for the 24 tests performed (corrected alpha required, 0.001). Results for comparison of genotype frequency are also shown in Tables 3A-B and were in the same direction for RGS2. There were no nominally significant findings in the other RGS genes.

TABLE 3B

SNPs associated with EPS

| Gene name, Chromosomal location/ Extent (bp) | dbSNP No. | SEQ ID NO: | PARK+ vs. PARK− p Allele (df 1) | PARK+ vs. PARK− p Genotype (df 2) |
|---|---|---|---|---|
| RGS2, 1q31 189,509,828- 189,513,063 | rs1933695 | 1 | 0.439 | 0.800 |
| | rs2179652 | 2 | 0.006 | 0.032 |
| | rs2746073 | 3 | 0.008 | 0.061 |
| | rs4606 | 4 | 0.0008* | 0.007* |
| | rs1819741 | 5 | 0.001* | 0.029 |
| | rs1152746 | 6 | 0.045 | 0.040 |
| RGS4, 1q23.3 159,770,809- 159,778,040 | rs951439 | | 0.901 | 0.756 |
| | rs6678136 | | 0.816 | 0.961 |
| | rs2842030 | | 0.904 | 0.592 |
| | rs10759 | | 0.561 | 0.802 |
| | rs2063142 | | 0.787 | 0.864 |
| RGS8, 1q25 179,347,449- 179,373,706 | rs3845459 | | 0.749 | 0.949 |
| | rs2023596 | | 0.521 | 0.962 |
| | rs4651129 | | 0.502 | 0.568 |
| | rs4652741 | | 0.490 | 0.512 |
| | rs567397 | | 0.057 | 0.046 |
| RGS9, 17q23-q24 60,564,054- 60,654,270 | rs1877822 | | 0.730 | 0.604 |
| | rs2869578 | | 0.567 | 0.880 |

TABLE 3A

SNPs examined in the RGS genes

| Gene name, Chromosomal location/ Extent (bp) | Database SNP No. | SNP Position on chromosome | Alleles (The variant bp is highlighted) | bp variation (Major, Minor) | Minor Allele Freq | SEQ ID NO: |
|---|---|---|---|---|---|---|
| RGS2, 1q31 189, 509, 828- 189, 513, 063 | rs1933695 | 189496477 | GAATTTATGGGAGTGGATAGT | G, C | 0.14 | 1 |
| | rs2179652 | 189501483 | TCCAGCCCTGTGGCCAGCCTC | T, A | 0.43 | 2 |
| | rs2746073 | 189510884 | TTGGTAAAAATGCGTTCAGCT | T, A | 0.28 | 3 |
| | rs4606 | 189512829 | CTATGTGCAACGGTATTGAAG | C, G | 0.27 | 4 |
| | rs1819741 | 189516495 | GAAATAAATATACCAAATTAA | T, A | 0.29 | 5 |
| | rs1152746 | 189528562 | CTTACTGTACATGCCACAGAA | A, T | 0.18 | 6 |
| RGS4, 1q23.3 159, 770, 809- 159, 778, 040 | rs951439 | 159765349 | | C, G | 0.43 | |
| | rs6678136 | 159768975 | | G, C | 0.43 | |
| | rs2842030 | 159772153 | | T, A | 0.48 | |
| | rs10759 | 159778009 | | C, G | 0.24 | |
| | rs2063142 | 159784947 | | T, A | 0.17 | |
| RGS8, 1q25 179, 347, 449- 179, 373, 706 | rs3845459 | 179352555 | | T, A | 0.37 | |
| | rs2023596 | 179354668 | | A, T | 0.37 | |
| | rs4651129 | 179357234 | | A, T | 0.37 | |
| | rs4652741 | 179358395 | | A, T | 0.38 | |
| | rs567397 | 179372295 | | A, T | 0.08 | |
| RGS9, 17q23-q24 60, 564, 054- 60, 654, 270 | rs1877822 | 60595539 | | T, A | 0.35 | |
| | rs2869578 | 60610219 | | C, G | 0.28 | |
| RGS10, 10q25 121, 249, 442- 121, 292, 157 | rs3009892 | 121239161 | | G, C | 0.29 | |
| | rs756279 | 121249869 | | A, T | 0.10 | |
| | rs7919216 | 121255625 | | T, A | 0.09 | |
| | rs1556591 | 121265893 | | A, T | 0.29 | |
| | rs1467813 | 121271597 | | G, C | 0.34 | |
| | rs7071853 | 121301596 | | T, A | 0.26 | |

TABLE 3B-continued

SNPs associated with EPS

| Gene name, Chromosomal location/ Extent (bp) | dbSNP | SEQ ID NO: | PARK+ vs. PARK− p Allele (df 1) | PARK+ vs. PARK− p Genotype (df 2) |
|---|---|---|---|---|
| RGS10, 10q25 121,249,442- 121,292,157 | rs3009892 | | 0.736 | 0.854 |
| | rs756279 | | 0.670 | 0.723 |
| | rs7919216 | | 0.895 | 0.917 |
| | rs1556591 | | 0.440 | 0.576 |
| | rs1467813 | | 0.624 | 0.890 |
| | rs7071853 | | 0.423 | 0.604 |

*Survives Bonferonni correction

Example 3

Linkage Disequilibrium and Haplotype Tagging SNPs in RGS2

Table 4 shows the degree of linkage disequilibrium (LD) between SNPs within and flanking RGS2. D' values are shown above the diagonal and $r^2$ values below the diagonal. An LD block was identified in RGS2 (according to the confidence interval algorithm of Gabriel et al, (Science 2002; 296:2225-2229), which encompasses rs2179652, rs2746073, rs4606 and rs1819741, in SEQ ID NOS. 2-5. The haplotype tagging SNPs (htSNPs) identified within the block were rs2179652 within SEQ ID NO:2, rs4606 within SEQ ID NO:4 and rs1819741 within SEQ ID NO:5.

TABLE 4

Linkage disequilibrium (LD) between SNPs within and flanking RGS2

| SNP/SEQ ID NO. | rs1933695/1 | rs2179652/2 | rs2746073/3 | rs4606/4 | rs1819741/5 | rs1152746/6 |
|---|---|---|---|---|---|---|
| rs1933695/1 | | 1.00 | 1.00 | 1.00 | 1.00 | 0.04 |
| rs2179652/2 | 0.13 | | 1.00 | 1.00 | 1.00 | 0.31 |
| rs2746073/3 | 0.06 | 0.34 | | 0.97 | 1.00 | 0.25 |
| rs4606/4 | 0.06 | 0.31 | 0.87 | | 0.97 | 0.39 |
| rs1819741/5 | 0.07 | 0.36 | 1.00 | 0.92 | | 0.45 |
| rs1152746/6 | 0.00 | 0.03 | 0.01 | 0.01 | 0.02 | |

Haplotype analysis was performed on the three tagging SNPs and the two flanking SNPs not included in the block (rs1933695, upstream of the block and rs152746, downstream the block; Table 5). The haplotype, GCCTG, also termed herein RGS2-HAP+, was significantly over-represented among PARK+ patients (PARK+:PARK− ratio 0.20: 0.08, p=0.0085; required alpha by Bonferonni correction, 0.01). RGS2-HAP+ is spanned along chromosome 1 in a region of approximately 40 Kbp, from nucleotide no. 189491443 to nucleotide no. 189531442 (FIG. 1), having the nucleotide variations as detailed in Tables 5, 6A and 6B, namely, guanine at position 189496477 (SNP No. rs1933695), cytosine at position 189501483 (SNP No. rs2179652), cytosine at position 189512829 (SNP No. rs4606), thymine at position 189516495 (SNP No. rs1819741) and guanine at position 189528562 (SNP No. rs1152746). Haplotypes of less than 5% frequency were excluded from the analysis.

In addition, a GTGCA haplotype, also termed herein RGS2-HAP−, was significantly over represented in PARK− patients after two-weeks antipsychotic treatment (PARK+: PARK− ratio 0.10:0.30, p=0.0017, required alpha by Bonferonni correction, 0.01). RGS2-HAP− is spanned along a region of approximately 40 Kbp, from nucleotide no. 189491443 to nucleotide no. 189531442, of chromosome 1 (FIG. 1) comprising the polymorphism detailed in Table 5, 7A and 7B namely, guanine at position rs1933695 (SNP No. rs1933695), thymine at position 189501483 (SNP No. rs2179652), guanine at position 189512829 (SNP No. rs4606), cytosine at position 189516495 (rs1819741) and adenine at position 189528562 (SNP No. rs1152746).

TABLE 5

Haplotype association with Parkinsonism

| Haplotype | Frequency | Case control ratio PARK+:PARK− | Chi Square | p Value |
|---|---|---|---|---|
| GCCTA | 0.35 | 0.41, 0.32 | 1.29 | 0.2560 |
| GTGCA (RGS2-HAP−) | 0.25 | 0.10, 0.30 | 9.84 | 0.0017 * |
| GTCTA | 0.11 | 0.15, 0.10 | 1.06 | 0.3029 |
| GCCTG (RGS2-HAP+) | 0.11 | 0.20, 0.08 | 6.92 | 0.0085 * |
| ATCTA | 0.11 | 0.09, 0.11 | 0.20 | 0.6531 |

* Survives Bonferonni correction for 5 tests (alpha = 0.01).

In order to further explore association of haplotypes in the RGS2 gene with Parkinsonism due to antipsychotic treatment, we analyzed all possible 2, 3, 4 and 5 SNP consecutive haplotypes across the gene. Haplotypes that were over-represented in PARK+ compared to PARK− patients and nominally significant (p<0.05) are shown in Tables 6A-B. Haplotypes associated with PARK− are shown in Tables 7A-B. Each of these tables encompasses the alleles making up the 5-SNP haplotypes that were significant on our initial test (RGS2-HAP− corresponding to GTGCA and RGS2-HAP+ corresponding to GCCTG, respectively). As is clear from Tables 6B and 7B, haplotypic association of RGS2 with development of Parkinson symptoms on treatment with antipsychotic drugs, spans the entire gene.

TABLE 6A

Over-represented haplotypes in PARK+ patients

| rs1933695 | rs2179652 | rs2746073 | rs4606 | rs1819741 | rs1152746 | Haplotype No. |
|---|---|---|---|---|---|---|
| G | C | | | | | 1 |
| G | C | T | | | | 2 |
| G | C | T | C | | | 3 |
| G | C | T | C | T | | 4 |
| G | C | T | C | T | G | 5 |
| | C | T | | | | 6 |
| | C | T | C | | | 7 |
| | C | T | C | T | | 8 |
| | C | T | C | T | G | 9 |
| | | T | C | | | 10 |
| | | T | C | T | | 11 |
| | | T | C | T | G | 12 |
| | | | C | T | | 13 |
| | | | C | T | G | 14 |
| | | | | T | G | 15 |

TABLE 6B

Haplotypes over-represented in PARK+ patients

| Haplotype No. | Frequency | Case control ratio PARK+:PARK− | Chi Square | p Value |
|---|---|---|---|---|
| 1 | 0.44 | 0.58, 0.39 | 7.01 | 0.0081 |
| 2 | 0.45 | 0.59, 0.40 | 6.89 | 0.0087 |
| 3 | 0.45 | 0.59, 0.40 | 6.90 | 0.0086 |
| 4 | 0.46 | 0.60, 0.40 | 7.37 | 0.0066 |
| 5 | 0.11 | 0.20, 0.08 | 6.71 | 0.0096 |
| 6 | 0.44 | 0.58, 0.39 | 6.67 | 0.0098 |
| 7 | 0.44 | 0.58, 0.39 | 6.68 | 0.0098 |
| 8 | 0.44 | 0.58, 0.39 | 6.68 | 0.0097 |
| 9 | 0.11 | 0.19, 0.074 | 6.47 | 0.011 |
| 10 | 0.72 | 0.861, 0.66 | 8.12 | 0.0044 |
| 11 | 0.70 | 0.84, 0.64 | 8.01 | 0.0047 |
| 12 | 0.14 | 0.22, 0.11 | 3.89 | 0.0486 |
| 13 | 0.71 | 0.87, 0.64 | 10.99 | 0.0009 |
| 14 | 0.15 | 0.23, 0.11 | 5.22 | 0.0224 |
| 15 | 0.14 | 0.23, 0.11 | 5.08 | 0.0242 |

TABLE 7A

Over-represented haplotypes in PARK− patients

| rs1933695 | rs2179652 | rs2746073 | rs4606 | rs1819741 | rs1152746 | Haplotype No. |
|---|---|---|---|---|---|---|
| G | T | | | | | 16 |
| G | T | A | | | | 17 |
| G | T | A | G | | | 18 |
| G | T | A | G | C | | 19 |
| G | T | A | G | C | A | 20 |
| | T | A | | | | 21 |
| | T | A | G | | | 22 |
| | T | A | G | C | | 23 |
| | T | A | G | C | A | 24 |
| | | A | G | | | 25 |
| | | A | G | C | | 26 |
| | | A | G | C | A | 27 |
| | | | G | C | | 28 |
| | | | G | C | A | 29 |
| | | | | C | A | 30 |

TABLE 7B

Haplotypes over-represented in PARK− patients

| Haplotype No. | Frequency | Case control ratio PARK+:PARK− | Chi Square | p Value |
|---|---|---|---|---|
| 16 | 0.427 | 0.308, 0.471 | 4.743 | 0.0294 |
| 17 | 0.292 | 0.163, 0.342 | 6.926 | 0.0085 |
| 18 | 0.267 | 0.117, 0.325 | 9.826 | 0.0017 |
| 19 | 0.273 | 0.114, 0.332 | 10.503 | 0.0012 |
| 20 | 0.244 | 0.109, 0.297 | 8.542 | 0.0035 |
| 21 | 0.285 | 0.154, 0.335 | 7.232 | 0.0072 |
| 22 | 0.261 | 0.112, 0.319 | 9.923 | 0.0016 |
| 23 | 0.275 | 0.126, 0.333 | 9.521 | 0.002 |
| 24 | 0.242 | 0.113, 0.291 | 7.559 | 0.006 |
| 25 | 0.255 | 0.103, 0.316 | 9.834 | 0.0017 |
| 26 | 0.275 | 0.127, 0.333 | 9.521 | 0.002 |
| 27 | 0.246 | 0.113, 0.296 | 7.88 | 0.005 |
| 28 | 0.277 | 0.127, 0.335 | 9.627 | 0.0019 |
| 29 | 0.25 | 0.109, 0.305 | 9.098 | 0.0026 |
| 30 | 0.267 | 0.108, 0.326 | 10.258 | 0.0014 |

Example 4

A Comparison Between Treatments—Antipsychotics Alone or in Combination With the Atypical Antipsychotic Risperidone Separate analyses were performed of the patients treated with TYP or with TYP-R. The same five SNPs in RGS2 that were associated with development or worsening of parkinsonism in the combined TYP and TYP-R groups were associated with this phenotype in the TYP group alone (rs2179652, p=0.0022; rs2746073, p=0.0068; rs4606, p=0.0023; rs1819741, p=0.0035; rs1152746, p=0.0138). The 5 SNP haplotype, RGS2-HAP+ (GCCTG) that was over-represented in the PARK+ patients in the combined group was also over-represented in PARK+ patients in the TYP group alone (PARK+:PARK− ratio 0.24:0.02, $x^2$=16.865, p=0.00004). The 5 SNP "protective" haplotype, RGS2-HAP− (GTGCA), that was over-represented in the PARK− patients in the combined group was over-represented in the PARK− patients in the TYP group alone (PARK+:PARK− ratio 0.08: 0.34, $x^2$=9.02, p=0.0027). There were no significant associations of single SNPs or haplotypes with development or worsening of Parkinsonism in the TYP-R group.

Example 5

Association of RGS Genes With Akathisia During Antipsychotic Treatment

To study the association of RGS genes with development or worsening of akathisia during the two weeks of antipsychotic treatment, patients were divided into Akathisia+ (n=27) and Akathisia− (n=85) groups, according to BAS. The two groups did not differ on background or demographic features including age, gender, education, age at onset, age at first psychiatric hospitalization, cumulative psychiatric hospitalization, dose of typical antipsychotics and risperidone and other treatment details. Baseline BAS scores were similar in the two groups (Akathisia+=1.0+1.6, Akathisia−= 1.1±1.8). Of the 27 Akathisia+ patients, 16 were also PARK+ while 11 did not show an overlap between the two manifestations of EPS. For two SNPs in the RGS2 gene there were nominally significant differences in allele frequency between the Akathisia+ and Akathisia− patients (rs2746073: p=0.04, rs1819741: p=0.02). These differences do not survive Bonferonni correction for the 24 tests performed. There was a trend towards significance for two other SNPs (rs2179652: p=0.0583, rs4606: p=0.0944). No haplotypes were significantly associated with development of worsening of akathisia but a trend was found for the GCCTG ($x^2$=3.589, p=0.058) and GTGCA haplotypes ($x^2$=3.361, p=0.066) that were associated with development or worsening of Parkinsonism. No significant associations of the other RGS genes (RGS4, RGS8, RGS9 and RGS10) with treatment emergent akathisia were observed.

Example 6

Association of the RGS2 SNPs With Development of EPS in the U.S. Study Sample

There were no significant differences between PARK+ (n=141) and PARK− patients (n=43) as regards demographic and clinical data, such as age, sex, ethnic origin (AA or Caucasian) and type of antipsychotic treatment (Table 8). However, mean PANSS score was significantly higher among PARK+ compared to PARK− patients (P=0.00002) and PARK75% compared to PARK− patients (P=0.001). A similar difference was observed in the African-American sub-sample (PARK+ vs. PARK−, P=0.004; PARK75% vs. PARK−, P=0.015).

TABLE 8

Demographic and clinical features of patients with (PARK+) or without (PARK−) antipsychotic induced Parkinsonism, assessed by the Simpson Angus Scale (SAS)

| | A. Whole Sample | | | | B. African American sub-sample | | | |
|---|---|---|---|---|---|---|---|---|
| | PARK+ Mean/n (%) | SD | PARK− Mean/n (%) | SD | PARK+ Mean/n (%) | SD | PARK− Mean/n (%) | SD |
| Number | 141 (76.6) | | 43 (23.4) | | 83 (74.1) | | 29 (25.9) | |
| Age | 40.3 | 9.8 | 39.9 | 9.1 | 40.29 | 9.7 | 41.1 | 8.8 |
| Male Gender | 129 (93.5) | | 40 (95.2) | | 79 (95.2) | | 27 (93.1) | |
| Antipsychotic Treatment[1] | | | | | | | | |
| Typical | 36 (25.5) | | 8 (18.6) | | 23 (27.7) | | 7 (24.1) | |
| Risperidone | 32 (22.7) | | 14 (32.6) | | 23 (27.8) | | 10 (34.5) | |
| Olanzepine | 37 (26.2) | | 12 (27.9) | | 20 (24.1) | | 7 (24.1) | |
| Clozapine | 33 (23.4) | | 8 (18.6) | | 17 (20.5) | | 5 (17.2) | |
| Rating Scales | | | | | | | | |
| PANSS total | 70.7** | 17.3 | 59.9 | 12.0 | 68.7* | 15.2 | 59.4 | 12.4 |
| SAS total | 2.70** | 2.83 | 0 | 0 | 2.59** | 1.81 | 0 | 0 |
| BAS total | 1.028* | 1.649 | 0.314 | 1.05 | 0.687 | 1.175 | 0.397 | 1.256 |
| Ethnicity | | | | | | | | |
| African American | 83 (58.9) | | 29 (67.4) | | | | | |
| Hispanic | 30 (21.3) | | 11 (25.6) | | | | | |
| White | 25 (17.7) | | 2 (4.7) | | | | | |
| Caucasian[2] | 55 (39.9) | | 13 (31) | | | | | |

*p < 0.01
**p < 0.0001
[1]Drug information missing for 3 patients in PARK+ and 1 in PARK− in the overall sample
[2]Hispanic + White
PANSS—Positive and Negative Symptoms scale;
SAS—Simpson Angus scale;
BAS—Barnes Akathisia scale Of the 4 SNPs that were suitable for association testing in the sample as a whole (no allele frequency differences between African American and Caucasian patients), one (rs4606), was associated with AIP (P=0.033) at a nominally significant level, the minor (G) allele being more frequent in the PARK− compared to the PARK+ group (Table 9A). When comparing the PARK− and the PARK75% groups, the significance level was stronger for rs4606 (P=0.016) and rs181974 emerged as nominally significant (P=0.046) (Table 9B).

TABLE 9A

SNP association with Parkinsonism

| Alleles Major, Minor | MinAF PARK+ | MinAF PARK− | PARK+ vs. PARK− P Allele (d.f. 1) | PARK+ vs. PARK− P Genotype (d.f. 2) |
|---|---|---|---|---|
| T, C | 0.44 | 0.42 | 0.697 | 0.633 |
| C, G | 0.27 | 0.39 | 0.033 | 0.043 |
| T, C | 0.24 | 0.33 | 0.091 | 0.169 |
| A, G | 0.25 | 0.34 | 0.116 | 0.241 |
| G, A | 0.04 | 0.07 | 0.372 | 0.286 |
| T, C | 0.42 | 0.37 | 0.505 | 0.410 |
| T, A | 0.08 | 0.07 | 0.919 | 0.809 |
| C, G | 0.27 | 0.43 | 0.027 | 0.023 |
| T, C | 0.22 | 0.36 | 0.046 | 0.040 |
| A, G | 0.27 | 0.30 | 0.654 | 0.575 |

TABLE 9B

SNP Association with Parkinsonism

| Alleles Major, Minor | MinAF PARK75% | PARK−75% vs. PARK− P Allele (d.f. 1) | PARK−75% vs. PARK− P genotype (d.f. 2) |
|---|---|---|---|
| T, C | 0.45 | 0.643 | 0.847 |
| C, G | 0.24 | 0.016 | 0.021 |
| T, C | 0.20 | 0.026 | 0.064 |
| A, G | 0.31 | 0.613 | 0.817 |
| G, A | | | |
| T, C | 0.05 | 0.628 | 0.460 |
| T, A | 0.37 | 0.967 | 1.000 |
| C, G | 0.05 | 0.592 | 0.439 |
| T, C | 0.23 | 0.025 | 0.027 |
| A, G | 0.18 | 0.034 | 0.024 |

Figure 2A:
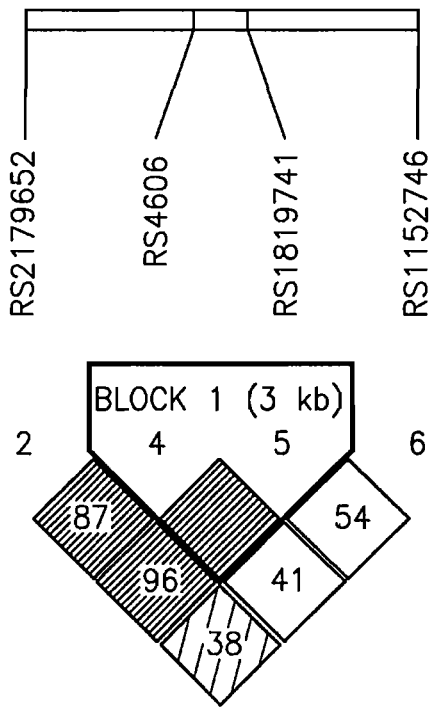
FIG. 2 schematically shows linkage disequilibrium between SNPs within and flanking RGS2, in the overall US sample (FIG. 2A) and the African-American sub-sample (FIG. 2B). LD blocks, defined by confidence intervals are marked.
Figure 2B:
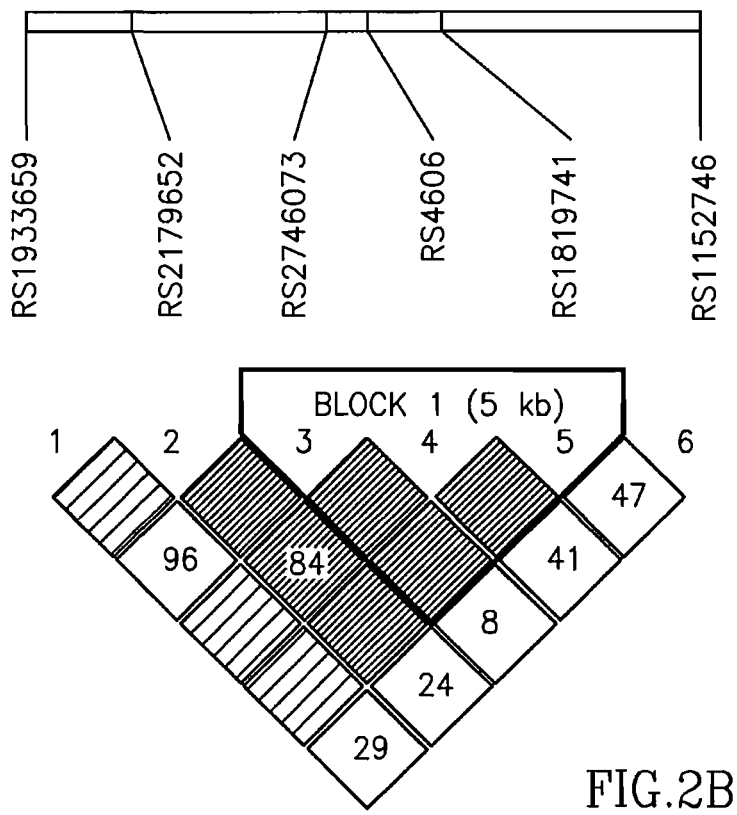

Haplotype analysis was performed encompassing all 4 SNPs. Two of the SNPs (rs4606 and rs181974) are in a LD block, according to the confidence interval algorithm of Gabriel et al (2002) (FIG. 2). As shown in Table 10, the haplotype CCTA (made up of rs2179652-C, rs4606-C, rs1819741-T and rs152746-A), was overrepresented among PARK+ (PARK+:PARK− ratio, 0.28:0.13, P=0.006) and PARK75% patients (PARK75%:PARK− ratio 0.24:0.10, P=0.016). The TGCA haplotype (made up of rs2179652-T, rs4606-G, rs1819741-C and rs152746-A) was overrepresented among PARK− patients (PARK+:PARK− ratio, 0.20:0.30, P=0.047; PARK75%:PARK− ratio, 0.16:0.31, P=0.013). The CCTG haplotype (made up of made up of rs2179652-C, rs4606-C, rs1819741-T and rs152746-G) was also overrepresented among PARK− patients (PARK+:PARK− ratio, 0.15:0.25; P=0.024) but the difference did not emerge as significant for the PARK75%:PARK− ratio (0.19:0.27, P=0.194).

Separate analyses were performed on the patients of AA origin, taking into account all 6 SNPs genotyped. As shown in Table 9 (A-B), the same two SNPs that were significant in the overall sample, rs4606 and rs1819741, were associated with AIP in the AA sub-sample, when allele frequencies were compared in the PARK+:PARK− and PARK75%:PARK− groups (rs4606: P=0.027, P=0.025; rs1918741: P=0.046, P=0.034). Haplotypes were extracted encompassing the same 5 SNPs as in our previous study (Greenbaum et al, 2007) and association to AIP was examined. Three of these SNPs (rs2746073, rs4606 and rs181974) are in an LD block (FIG. 1). As shown in Table 10, the haplotype GTGCA (made up of rs1933695-G, rs2179652-T, rs4606-G, rs1819741-C and rs152746-A) was overrepresented in the PARK− group (PARK+:PARK− ratio, 0.18:0.31, P=0.042; PARK75%: PARK− ratio 0.16:0.34, P=0.025). The GCCTA haplotype was overrepresented in PARK+ vs. PARK− patients (P=0.049) and the GTCTA haplotype was in PARK75% vs. PARK− patients (P=0.032). None of these univariant analyses survived Bonferonni correction for multiple testing.

TABLE 10

Frequency of haplotypes in the RGS2 gene and their association with Parkinsonism

| Haplotype | Frequency | Case Control Frequency PARK+:PARK− | X2 | p-Value | Case Control Frequency PARK-75%: PARK− | X2 | p-Value |
|---|---|---|---|---|---|---|---|
| Overall Sample | | | | | | | |
| CCTA | 0.24 | 0.28:0.13 | 7.68 | 0.006 | 0.24:0.10 | 5.81 | 0.016 |
| TCTA | 0.24 | 0.25:0.19 | 1.32 | 0.250 | 0.28:0.20 | 1.42 | 0.233 |
| TGCA | 0.22 | 0.20:0.30 | 3.95 | 0.047 | 0.16:0.31 | 6.21 | 0.013 |
| CCTG | 0.17 | 0.15:0.25 | 5.13 | 0.024 | 0.19:0.27 | 1.69 | 0.194 |
| TCTG | 0.05 | 0.05:0.03 | 0.56 | 0.454 | 0.06:0.03 | 1.07 | 0.302 |

TABLE 10-continued

Frequency of haplotypes in the RGS2 gene and their association with Parkinsonism

| Haplotype | Frequency | Case Control Frequency PARK+:PARK- | X2 | p-Value | Case Control Frequency PARK-75%: PARK- | X2 | p-Value |
|---|---|---|---|---|---|---|---|
| African Americans | | | | | | | |
| GCCTA | 0.25 | 0.28:0.15 | 3.85 | 0.049 | 0.20:0.10 | 2.16 | 0.141 |
| GTGCA | 0.22 | 0.18:0.31 | 4.12 | 0.042 | 0.16:0.34 | 4.99 | 0.025 |
| GTCTA | 0.20 | 0.23:0.14 | 2.07 | 0.150 | 0.31:0.14 | 4.58 | 0.032 |
| GCCTG | 0.14 | 0.12:0.18 | 1.07 | 0.300 | 0.12:0.21 | 1.42 | 0.232 |
| GTCTG | 0.05 | 0.06:0.04 | 0.17 | 0.678 | 0.09:0.06 | 0.50 | 0.478 |

P < 0.05 is marked in bold font.

To perform a uniform test of haplotypes across all samples, we examined the association with AIP of the 4 SNP haplotypes that were significantly associated in the overall US sample, in the AA sub-sample and in the Israeli sample reported in our previous publication (Greenbaum et al, 2007). Results are shown in Table 11. The TGCA haplotype, which has a frequency range of 0.218-0.248, was overrepresented in the PARK- group across all samples by a margin of 10-14%. Results for the CCTA and CCTG haplotypes were less consistent among the three samples.

TABLE 11

Frequency of 4 SNP haplotypes in the RGS2 gene in PARK+ vs. PARK- patients

| Sample | Frequency | Case Control Frequency PARK+: PARK- | x2 | p Value |
|---|---|---|---|---|
| CCTA | | | | |
| Overall US sample | 0.24 | 0.13:0.28 | 7.679 | 0.006 |
| African Americans | 0.243 | 0.144:0.276 | 3.986 | 0.046 |
| Israeli sample | 0.347 | 0.342:0.360 | 0.061 | 0.805 |
| TGCA | | | | |
| Overall US sample | 0.22 | 0.30:0.20 | 3.948 | 0.047 |
| African Americans | 0.218 | 0.317:0.184 | 4.373 | 0.037 |
| Israeli sample | 0.248 | 0.298:0.127 | 6.832 | 0.009 |
| CCTG | | | | |
| Overall US sample | 0.17 | 0.25:0.15 | 5.128 | 0.024 |
| African Americans | 0.142 | 0.182:0.128 | 1.026 | 0.311 |
| Israeli sample | 0.122 | 0.080:0.226 | 8.708 | 0.003 |

P <0.05 is marked in bold font.

Logistic regression analysis, controlling for age, gender and PANSS scores (Table 12) emphasizes the significant protective effect of the rs4606 G allele against AIP in the Israeli and US samples and the African-American sub-sample. Carriers of the rs4606 G allele (as heterozygotes or homozygotes) were 3.2-5.3 times less likely to be in the PARK+ group. The effect of the TGCA haplotype was similar but weaker, particularly in the Israeli sample.

In contrast to AIP, no association of SNPs or haplotypes in the RGS2 gene with antipsychotic-induced akathisia, as measured by the BAS, was observed.

TABLE 12

Protective effect of RGS2-rs4606 G allele and RGS2-TGCA haplotype against antipsychotic-induced Parkinsonism

| | PARK+ | PARK- | 1/Odds Ratio | 95% CI | p Value |
|---|---|---|---|---|---|
| rs4606 G Allele Carriers | | | | | |
| Israeli Sample | 0.25 | 0.51 | 3.03 | 0.92-0.12 | 0.034 |
| US Overall Sample* | 0.45 | 0.67 | 4.50 | 0.52-0.01 | 0.001 |
| African-American Sub-Sample* | 0.43 | 0.71 | 5.26 | 0.56-0.07 | 0.002 |
| TCCA Haplotype Carriers | | | | | |
| Israeli Sample | 0.27 | 0.49 | 2.44 | 1.10-0.16 | 0.079 |
| US Overall Sample* | 0.38 | 0.58 | 3.23 | 0.66-0.14 | 0.003 |
| African-American Sub-Samples | 0.32 | 0.59 | 4.17 | 0.63-0.09 | 0.004 |

*Analysis control for PNASS scores

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for identifying a human subject as having a decreased tendency to develop Parkinsonism as an extrapyramidal symptom following treatment with an antipsychotic drug, said method comprising:
   obtaining a sample comprising genetic material of said subject;
   detecting, in said genetic material, the presence of at least one allele of the regulator of G-protein signaling 2 gene, comprising guanine at the SNP rs4606 thereby identifying the human subject as having a decreased tendency to develop Parkinsonism as an extrapyramidal symptom following treatment with an antipsychotic drug; and
   treating said human subject with a typical antipsychotic drug wherein detecting, in said genetic material, the presence of at least one allele of the regulator of G-protein signaling 2 gene is attained by a technique selected from the group consisting of: terminator sequencing, restriction digestion, allele-specific polymerase reaction, single-stranded conformational polymorphism analysis, genetic bit analysis, temperature gradient gel electrophoresis ligase chain reaction and ligase/polymerase genetic bit analysis.

2. The method of claim 1 further comprising detecting, in said genetic material of said human subject, the presence of thymine in at least one of rs2746073 and rs1819741.

3. The method of claim 1, wherein the sample is obtained from a biological specimen selected from the group consisting of: blood, saliva, urine, sweat, buccal material, skin and hair.

4. The method of claim 1, wherein detecting, in said genetic material, the presence of at least one allele of the regulator of G-protein signaling 2 gene is attained by employing nucleotides with a detectable characteristic selected from the group consisting of inherent mass, electric charge, electric spin, mass tag, radioactive isotope type bioluminescent molecule, chemiluminescent molecule, nucleic acid molecule, hapten molecule, protein molecule, light scattering/phase shifting molecule and fluorescent molecule.

5. The method of claim 1, wherein the subject is psychotic.

6. The method of claim 1, wherein said method is preformed prior to initiation of treatment with a composition comprising a typical antipsychotic drug.

7. The method of claim 1, wherein the typical antipsychotic drug is selected from the group consisting of: zuclopenthixol, haloperidol, perphenazine, fluphenazine, flupenthixol, levomepromazine, chlorpromazine, penfluridol, pimozide, molindone, thiothixene, thioridazine, trifuoperazine, loxapine, prochlorperazine and combinations thereof.

8. The method of claim 1, wherein the treatment with an antipsychotic drug further comprises treatment with at least one atypical antipsychotic drug.

9. The method of claim 8, wherein the at least one atypical antipsychotic drug is risperidone.

10. The method of claim 1, further comprising repeating the detecting step.

11. A method for identifying a human subject as having an increased tendency to develop, or resist the development of, Parkinsonism as an extrapyramidal symptom following treatment with an antipsychotic drug, the method comprising:
   obtaining a sample comprising genetic material of said subject; and
   (i) detecting, in said genetic material, the presence of at least one allele of the regulator of G-protein signaling 2 gene, comprising guanine at the SNP rs4606; and correlating the presence of the detected at least one guanine allele at rs4606 with an increased tendency of said subject to resist the development of Parkinsonism as an extrapyramidal symptom following treatment with an antipsychotic drug; or
   (ii) detecting, in said genetic material, the presence of two alleles of the regulator of G-protein signaling 2 gene, comprising cytosine at the SNP rs4606; and correlating the presence of the detected two cytosine alleles at rs4606 with an increased tendency of said subject to develop Parkinsonism as an extrapyramidal symptom following treatment with an antipsychotic drug
   wherein detecting, in said genetic material, the presence of at least one allele of the regulator of G-protein signaling 2 gene is attained by a technique selected from the group consisting of: terminator sequencing, restriction digestion, allele-specific polymerase reaction, single-stranded conformational polymorphism analysis, genetic bit analysis, temperature gradient gel electrophoresis ligase chain reaction and ligase/polymerase genetic bit analysis.

* * * * *